(12) United States Patent
Graef et al.

(10) Patent No.: US 7,125,470 B2
(45) Date of Patent: Oct. 24, 2006

(54) UNITARY STRATIFIED COMPOSITE

(75) Inventors: Peter A. Graef, Puyallup, WA (US); Colin Elston, Gig Harbor, WA (US); Daniel T. Bunker, Karhula (FI); Fred B. Howard, Olalla, WA (US); Jeffrey D. Mathews, Puyallup, WA (US); Shahrokh A. Naieni, Seattle, WA (US); Charles E. Miller, Kent, WA (US)

(73) Assignee: National Institute for Strategic Technology Acquisitions and Commercialization, Manhattan, KS (US)

(*) Notice: Subject to any disclaimer, the term of this patent is extended or adjusted under 35 U.S.C. 154(b) by 75 days.

(21) Appl. No.: 10/294,242

(22) Filed: Nov. 13, 2002

(65) Prior Publication Data

US 2003/0130633 A1 Jul. 10, 2003

Related U.S. Application Data

(60) Division of application No. 09/137,503, filed on Aug. 20, 1998, now abandoned, which is a continuation of application No. PCT/US97/22342, filed on Dec. 5, 1997.

(60) Provisional application No. 60/032,916, filed on Dec. 6, 1996.

(51) Int. Cl.
*D21F 11/04* (2006.01)
*D21H 21/22* (2006.01)

(52) U.S. Cl. ............ 162/129; 162/125; 162/127; 162/146; 162/207

(58) Field of Classification Search ............ 162/146, 162/129, 123, 125, 127, 157.6, 158, 157.2, 162/204, 207; 428/152–154; 604/365–367, 604/370, 374, 375, 378
See application file for complete search history.

(56) References Cited

U.S. PATENT DOCUMENTS

| | | | | |
|---|---|---|---|---|
| 2,414,833 A | * | 1/1947 | Osborne | 162/129 |
| 3,384,537 A | * | 5/1968 | Keller | 162/129 |
| 3,455,778 A | * | 7/1969 | Bernardin | 162/113 |
| 3,674,621 A | * | 7/1972 | Miyamoto et al. | 162/146 |
| 4,012,281 A | * | 3/1977 | Mayer et al. | 162/127 |
| 4,154,883 A | * | 5/1979 | Elias | 162/129 |
| 4,963,230 A | * | 10/1990 | Kawase et al. | 162/129 |
| 5,102,501 A | * | 4/1992 | Eber et al. | 162/129 |
| 5,167,765 A | * | 12/1992 | Nielsen et al. | 162/146 |
| 5,238,534 A | * | 8/1993 | Manning et al. | 162/146 |
| 5,409,572 A | * | 4/1995 | Kershaw et al. | 162/109 |
| 5,437,418 A | * | 8/1995 | Graef et al. | 241/65 |
| 5,607,550 A | * | 3/1997 | Akers | 162/102 |
| 5,629,069 A | * | 5/1997 | Hamajima et al. | 428/154 |
| 5,843,055 A | * | 12/1998 | Seger | 604/365 |
| 6,277,241 B1 | * | 8/2001 | Merker et al. | 162/111 |

* cited by examiner

*Primary Examiner*—Eric Hug
(74) *Attorney, Agent, or Firm*—Gregory J. Skoch

(57) ABSTRACT

A unitary stratified composite composed of a first stratum and a second stratum integrally connected by a transition zone is disclosed. The first stratum serves as a liquid acquisition stratum that rapidly acquires and then transfers liquid to the second stratum. The second stratum serves to withdraw liquid from the first stratum and further serves as a temporary storage stratum. Methods for forming the unitary stratified composite are also disclosed.

12 Claims, 11 Drawing Sheets

UNITARY STRATIFIED COMPOSITE

CROSS-REFERENCES TO RELATED APPLICATIONS

This application is a divisional of U.S. Application Ser. No. 09/137,503, filed Aug. 20, 1998, now abandoned, which is a continuation of International Application No. PCT/US97/22342, filed Dec. 5, 1997, which claims the benefit of U.S. Provisional Patent Application No. 60/032,916, filed Dec. 6, 1996, priority of the filing dates of which is hereby claimed under 35 U.S.C. §§ 120 and 119, respectively. Each of these applications is incorporated herein by reference.

FIELD OF THE INVENTION

The present invention relates to an absorbent composite and methods for making the same and, more particularly, to a unitary stratified composite having a first stratum and a second stratum integrally connected by a transition zone.

BACKGROUND OF THE INVENTION

Cellulose fibers derived from wood pulp are used in a variety of absorbent articles, for example, diapers, incontinence products, and feminine hygiene products. It is desirable for the absorbent articles to have a high absorbent capacity for liquid, as well as to have good dry and wet strength characteristics for durability in use and effective fluid management. In addition to absorbent capacity, the ability to rapidly absorb a liquid is a desirable characteristic of an absorbent article. For example, diapers and other hygienic products that do not contain a dedicated liquid acquisition component, suffer from liquid leakage and rewet (i.e., the feeling of dampness to touch after use). Hygienic products that contain only a high loft nonwoven acquisition layer suffer from a lack of fast temporary liquid storage capability and leakage. Hygienic products that contain cellulose-based acquisition layers suffer from rewet due to the temporary storage capability of the cellulose's fibers and lack of complete drainage. Further, cellulose-based acquisition materials have poor wet and dry integrity.

One solution to the problem of providing absorbent articles that possess the advantageous properties of high absorbent capacity, rapid liquid acquisition, reduced leakage, and superior rewet performance has been the production of absorbent articles that contain multiple layers. For example, the combination of one layer having rapid liquid acquisition characteristics with another layer having high absorbent capacity results in a product that offers the advantages of both strata. Some improvements in the performance of products that include multiple layers have been directed to the integration of the layers. Approaches to increased integration typically include methods of bonding one layer to the next. Increasing the commingling between, for example, a liquid acquisition layer and a liquid storage layer can increase fluid communication and the rate and drainage efficiency at which the acquisition layer releases liquid to the storage layer, thereby increasing the product's overall liquid containment capability.

Despite the advantages associated with multiply layered absorbent products, problems related to the effective layer-to-layer fluid communication of diverse materials, and the economic costs of producing, handling, and bonding individual component layers remain.

Accordingly, there exists a need for an integrated absorbent material that provides the dry feel and rapid liquid acquisition of a high-loft, nonwoven material, and rapid temporary storage capability and rapid liquid acquisition performance of cellulose fibers such as crosslinked cellulose pad. The present invention seeks to fulfill these needs and provides further related advantages.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE PREFERRED EMBODIMENT

In one aspect, the present invention provides an absorbent composite that is a unitary stratified composite. The composite is stratified in that the composite includes strata or layers, and unitary in that the strata are integrally connected through a transition zone to provide two strata in intimate fluid communication. Generally, the absorbent composite is composed of a first stratum that includes a hydrophobic fibrous material that does not absorb bodily fluids and which forms an open and bulky stratum having a relatively low basis weight, and a second stratum that includes a hydrophilic fibrous material, such as crosslinked cellulose fibers, and having a basis weight preferably greater than the first stratum. Either one or both strata can also include a binder to effect bonding between the fibers of the first stratum, between the fibers of the second stratum, and between the fibers of the top and second strata of the unitary stratified composite. The unitary stratified composite of the present invention can be incorporated into a variety of absorbent products and articles to provide rapid temporary storage capacity, to increase the liquid acquisition rate, to reduce leakage, and to improve the rewet and dry feel performance of the absorbent article.

In another aspect of the present invention, methods for producing a unitary stratified composite are provided. The methods of the present invention include wet laid, dry laid, and foam processes.

In another aspect, a preferred hygiene product converting process incorporating the unitary stratified composite of the present invention is provided.

Figure 1:
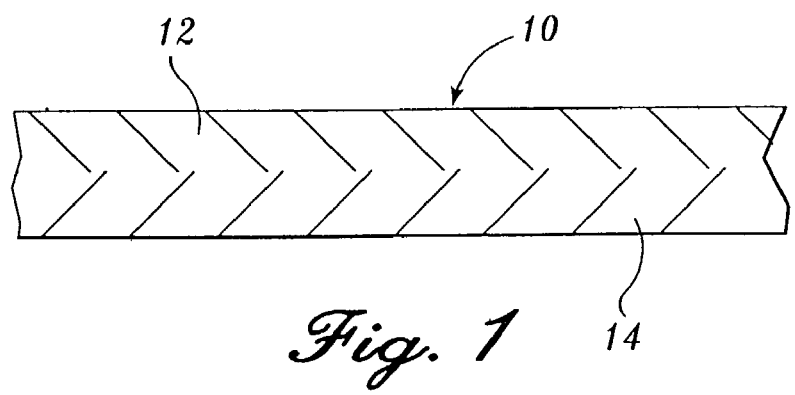
FIG. 1 is a schematic view of a representative unitary stratified composite produced in accordance with the present invention.

Referring to FIG. 1, the unitary stratified composite of the present invention, indicated generally by reference numeral 10, includes a first stratum 12 and a second stratum 14. The first stratum of the unitary stratified composite serves primarily as an acquisition stratum that can rapidly acquire liquid at the point of insult, and then rapidly and completely pass the liquid to the second stratum. The first stratum also serves as an antiwet back stratum having greater pore size and lower hydrophilicity than the second stratum. The second stratum serves to rapidly withdraw liquid from the first stratum and also serves as a temporary reservoir for the liquid gush associated with the release of bodily fluids. Representative composites of the invention formed in accordance with the present invention are shown in FIGS. 11–20. The substantially homogeneous individual fibrous strata are clearly apparent in FIGS. 11, 13, 15, and 17.

Figure 19:
FIG. 19 is a photomicrograph (12×magnification) of a transition zone of a representative unitary stratified composite produced by a foam-formed method in accordance with the present invention.
Figure 20:
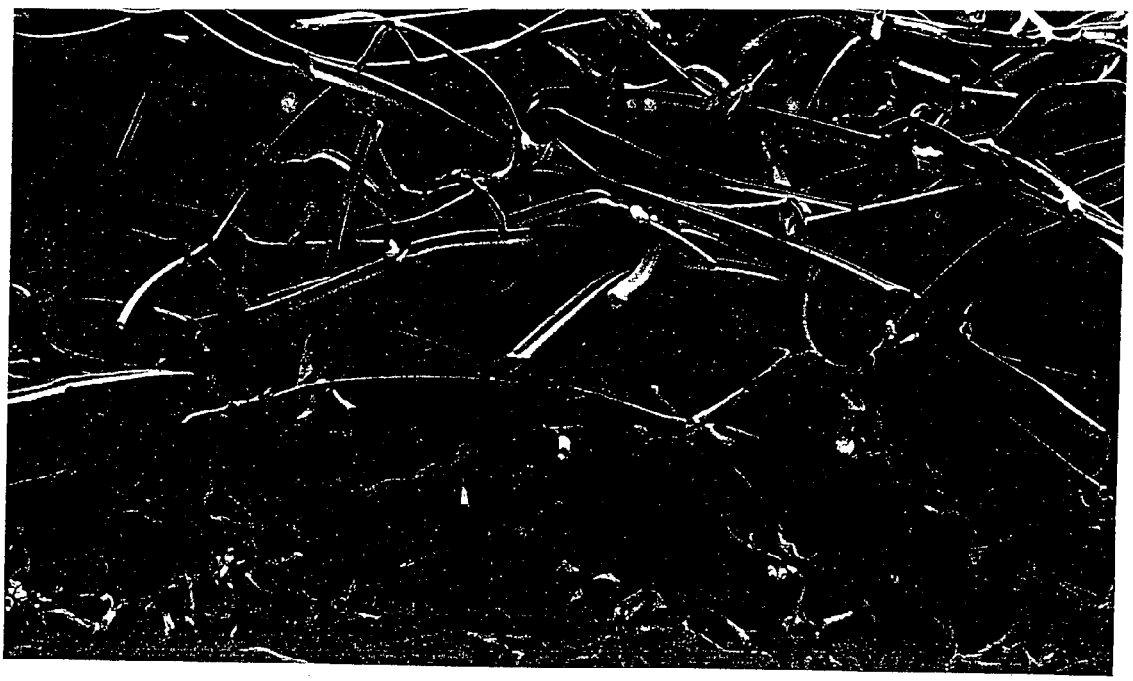
FIG. 20 is a photomicrograph (40×magnification) of the transition zone of the representative unitary stratified composite shown in FIG. 19.

The composite's transition zone, which integrally connects the first and second strata and provides for intimate fluid communication, includes fibers from one stratum extending into the other. The transition zone can include hydrophobic fibers extending from the first stratum into the second stratum, as well as hydrophilic fibers extending from the second stratum into the first stratum. While the first stratum may be substantially coextensive with the second stratum, the transition zone is substantially coextensive with at least one of the composite's stratum. The unitary stratified composite's transition zone is illustrated in FIGS. 11–20, which show representative composites formed in accordance with the present invention. Referring to these FIGURES, the transition zone is located in the composite generally between the substantially homogeneous regions of the individual strata and is defined as the. region of the composite where the fibers from one stratum are commingled with fibers from the other stratum. The transition zone is clearly illustrated in FIGS. 19 and 20, which show the commingling of fibers extending from one stratum into the other for representative composites formed by air-laid, wet-laid, and foam-formed methods, respectively. Referring to FIGS. 19 and 20, the composite's transition zone is characterized by the commingling of relatively smooth, tubular hydrophobic fibers (i.e., polyethylene terephthalate fibers) of the first stratum with the relatively kinked, ribbon-shaped hydrophilic fibers (i.e., crosslinked cellulosic fibers) of the second stratum.

The first stratum of the absorbent composite is generally a hydrophobic stratum that includes a hydrophobic fibrous material (i.e., one or more hydrophobic fibers). Other fibers, such as hydrophilic fibers, may be included in the first stratum as long as the overall first stratum remains relatively less hydrophilic than the second stratum. The first stratum can be composed of natural and/or synthetic fibers that do not significantly absorb bodily fluids, and that form an open (i.e., porous) and bulky stratum or web. The first stratum's pore size is preferably greater than the second stratum's and allows efficient fluid communication and drainage to the second stratum. Suitable synthetic fibers include, for example, polyethylene terephthalate (PET), polyethylene, polypropylene, nylon, latex, rayon. The synthetic fibers are present in an amount up to about 90% by weight of the first stratum. Suitable natural fibers include, for example, cotton, wool, wood pulp, straw, kenaf, and other cellulosic fibers. In a preferred embodiment, the cellulosic fibers are crosslinked cellulosic fibers present in an amount up to about 90% by weight. The fibers noted above can optionally include one or more additives, such as wet strength agents, sizing agents, and surface active agents. The fibers noted above are commercially available from a number of suppliers including Hoechst Celanese, DuPont, Eastman Chemical, Hercules, Danaklon, Inc., and Weyerhaeuser Company. In a preferred embodiment, the first stratum includes a synthetic fiber and, more preferably, the first stratum includes polyethylene terephthalate.

Generally, the greatest rate of liquid acquisition is attained with composites having relatively low density. The formation of low-density composites can be achieved by varying the individual components of the composite. The performance of the unitary stratified composite of the present invention is dependent upon a number of factors including the length, denier (g/m), crimping (crimps per inch), type of fiber treatment and physical and chemical nature of the fibers of the first stratum. Suitable fibers useful for construction of the first stratum have a length up to about 4 inches, and preferably have a length between about 0.25 and about 1.5 inches. Suitable fibers include fibers having denier up to about 40 denier, and preferably between about 5 and about 20 denier. While straight fibers can be advantageously used in the formation of the first stratum, in a preferred embodiment, the first stratum includes from about 50% to about 100% by weight of total crimped fibers. In a preferred embodiment, the fibers have up to about 30 crimps per inch and more preferably from about 1 to about 20 crimps per inch. In a most preferred embodiment, the first stratum includes 100% crimped fibers by weight of total fibers having from about 5 to about 15 crimps per inch. Thus, in a preferred embodiment, the first stratum includes polyethylene terephthalate fibers having relatively high denier, long length, and low crimp level.

In another preferred embodiment, the synthetic fibers include polyester fibers having morphologies other than the conventional homogeneous solid fibers noted above. Composites of the invention comprising hollow, deep-grooved, and lobal polyester fibers exhibit advantageous liquid acquisition characteristics. For example, deep-grooved fibers provide composites having low rewet, possibly due in part to improved capillary wicking in the grooves and more rapid liquid evaporation. Hollow fibers provide a composite having enhanced loft compared to composites that include homogeneous solid fibers. Lobal fibers (i.e., fibers having lobal cross-sectional shape) provide composites having a greater resistance to wet collapse compared to solid, round cross-sectioned fiber. For example, lobal polyester fibers are commercially available from Hoechst Celanese.

As noted above, the first stratum includes a binder. Suitable binders include, but are not limited to, cellulosic and synthetic fibrous materials, bonding agents, soluble bonding mediums, and wet strength agents as described below. In one preferred embodiment, the binder includes bicomponent binding fibers, such as Celbond® (Hoechst Celanese) and D-271P® (DuPont). In another preferred embodiment, the binder includes a soluble binding medium, more preferably cellulose acetate used in combination with the solvent triacetin and/or triethyl citrate. For embodiments of the first stratum that include a binder, the binder is included in the stratum in an amount ranging from about 10% to about 50% by weight of the components of the first stratum. Preferably, the binder is integrally incorporated into or onto the fibrous web that is formed in the production of the unitary stratified composite. The binder can be added to fibers prior to web formation, by applying the binder to the air-laid, wet-laid, or foam-formed web after web deposition, after drying, or a combination thereof.

Generally, the first stratum of the unitary stratified composite has a basis weight of about 10 to about 100 $g/m^2$. The density of the first stratum can range from about 0.01 to about 0.3 $g/cm^3$, and preferably from about 0.01 to about 0.08 $g/cm^3$.

The second stratum of the unitary stratified composite of the present invention can be a hydrophilic stratum relative to the first stratum and include a hydrophilic fibrous material (i.e., one or more hydrophilic fibers). The second stratum can also include other fibers, such as hydrophobic fibers (e.g., synthetic fibers such as polyester fibers including polyethylene terephthalate fibers), and these fibers can be included in the second stratum in an amount up to about 90% by weight of the stratum, provided that the overall stratum remains relatively hydrophilic compared to the first stratum. The second stratum can also include mixtures of hydrophilic and synthetic fibers. Further, the second stratum has smaller pores than the first stratum, thereby facilitating fluid communication between the strata and drainage from the first stratum. In a preferred embodiment, the hydrophilic fibers include cellulosic fibers in an amount up to about 90% by weight of the stratum, and more preferably crosslinked cellulosic fibers in an amount up to about 90% by weight of the stratum. In another preferred embodiment, the cellulosic fibers include chemithermomechanical pulp fibers. Suitable and preferred cellulosic fibers are described below.

Alternatively, in another embodiment, the second stratum does not include cellulosic fibers. In this embodiment, the stratum comprises synthetic fibers in an amount up to about 95% by weight and binder in an amount from about 5 to about 50% by weight.

To further improve storage capacity of the absorbent composite, in another embodiment the second stratum includes a superabsorbent polymeric material.

In addition to hydrophilic fibers, the second stratum also includes a binder. Suitable binders for the fibers of the second stratum include, but are not limited to, those noted above and described in more detail below. The binder is preferably present in an amount ranging from about 5% to about 50% by weight of the components of the second stratum.

The second stratum generally has a basis weight of from about 10 to about 500 $g/m^2$. The second stratum has a density from about 0.03 to about 0.5 $g/cm^3$, and preferably from about 0.03 to about 0.1 $g/cm^3$.

The second stratum is generally characterized as having a smaller pore size and increased hydrophilicity relative to the first stratum. Thus, the acquired liquid flows away from the first stratum to the more hydrophilic second stratum having smaller pores. Furthermore, because the pore size of the second stratum is less than the pore size of the first stratum, a pore size gradient is created that provides liquid drainage away from the first stratum. See, for example, FIGS. 11–18. The intimate commingling between the fibers of the first and second stratum of the unitary stratified composite of this invention provided by the transition zone enables more efficient drainage of the first stratum and fluid communication between the two strata than in other absorbent products formed from separate and distinct acquisition and storage layers.

The second stratum of the unitary stratified composite primarily serves to rapidly draw liquid from the first stratum. The second stratum also acts to temporarily store liquid acquired by the absorbent composite and prevent flow back to and beyond the first stratum. Depending upon the nature of the absorbent construct, an absorbent article incorporating the unitary stratified composite may include one or more additional strata, such as a permanent storage (see, for example, FIG. 2). In such a construct, in addition to rapidly absorbing the acquired liquid from the first stratum, the second stratum has absorbent capacity sufficient to temporarily hold the acquired liquid and therefore provide time sufficient for the core stratum to permanently absorb the liquid from the absorbent composite.

The unitary stratified composite is produced by forming a first stratum and a second stratum, each formulated as described above. In one embodiment, the overall absorbent composite includes a hydrophilic fibrous material (i.e., one or more hydrophilic fibers) present in the absorbent composite in an amount from about 40% to about 90% by weight of the total composite, a hydrophobic fibrous material (i.e., one or more hydrophobic fibers) present in the composite in an amount from about 1% to about 60% by weight of the total composite, and a binder present in the composite in an amount from about 5% to about 30% by weight of the total composite. Preferably, the hydrophilic fibers are present in the composite in about 60% to about 80% by weight of the total composite, the hydrophobic fibers are present in the composite in about 5% to about 20% by weight of the total composite, and a binder present in the composite in the amount of about 10% to about 20% by weight of the total composite.

The unitary stratified composite generally has a basis weight of from about 20 to about 600 $g/m^2$, and preferably from about 50 to about 360 $g/m^2$.

Generally, the absorbent composite has a density from about 0.01 to about 0.4 $g/cm^3$, and preferably from about 0.03 to about 0.15 $g/cm^3$. In one embodiment of the present invention, the unitary stratified composite is a densified composite. Densification methods useful in producing the densified composites of the present invention are well known to those in the art. Densified unitary stratified composites of this invention generally have a density from about 0.1 to about 0.5 $g/cm^3$, and preferably from about 0.1 to about 0.25 $g/m^3$.

Preferably, the unitary stratified composite of the invention is an undensified composite. Accordingly, production methods used in connection with the absorbent composite preferably do not include subjecting the absorbent composite, or absorbent articles that incorporate the absorbent composite, to densification conditions. For example, in the production of diapers that incorporate the absorbent composite of the present invention, the absorbent composite is preferably incorporated into the diaper after the diaper has been subjected to the application of pressure such as, for example, being passed through a calender roll.

The unitary stratified composite can be produced in a number of forms including sheets, rolls, boxes, and cartridges and having a variety of thicknesses.

As noted above, cellulosic fibers are the preferred basic component of the second stratum of unitary stratified composite of the present invention. Although available from other sources, cellulosic fibers are derived primarily from wood pulp. Suitable wood pulp fibers for use with the invention can be obtained from well-known chemical processes such as the Kraft and sulfite processes, whether bleached or unbleached. The pulp fibers may also be processed by thermomechanical, chemithermomechanical methods, or combinations thereof. The preferred pulp fiber is produced by chemical methods. Ground wood fibers, recycled or secondary wood pulp fibers, and bleached and unbleached wood pulp fibers can be used. The preferred starting material is prepared from long fiber coniferous wood species, such as southern pine, Douglas fir, spruce, and hemlock. Details of the production of wood pulp fibers are well-known to those skilled in the art. These fibers are commercially available from a number of companies, including Weyerhaeuser Company, the assignee of the present invention. For example, suitable cellulose fibers produced from southern pine that are usable with the present invention are available from Weyerhaeuser Company under the designations CF416, NF405, NB416, PL416, and FR516.

The wood pulp fibers useful in the present invention can also be pretreated prior to use with the presents invention. This pretreatment may include physical treatment, such as subjecting the fibers to steam, twisting or crimping and/or chemical treatment, for example, crosslinking the cellulose fibers using any of a variety of conventional crosslinking agents such as dimethyldihydroxyethyleneurea. Specifically, crosslinking wood pulp fibers increases their resiliency, and thereby can improve their absorbency. Crosslinked cellulose fibers and methods for their preparation are known in the art and are disclosed in, for example, U.S. Pat. No. 5,225,047, issued Jul. 6, 1993, entitled "Crosslinked Cellulose Products and Method For Their Preparation," expressly incorporated herein by reference. Suitable crosslinked cellulose fibers produced from southern pine are available from Weyerhaeuser Company under the designation NHB416.

Although not to be construed as a limitation, other examples of pretreating fibers include the application of fire retardants to the fibers, or treatments with surfactants or other liquids, such as water or solvents, which modify the surface of the fibers. See, for example, U.S. patent application Ser. No. 08/669,406, now U.S. Pat. No. 5,837,627, filed Jul. 3, 1996, and entitled "Fibrous Web Having Improved Strength and Method of Making the Same." Still other pretreatments include exposure to or incorporation of antimicrobials, pigments and densification or softening agents. Fibers pretreated with other chemicals, such as thermoplastic and thermosetting resins also may be used. Combinations of pretreatments also may be employed. Absorbent webs may also be similarly treated after web formation.

Any of the previously noted cellulosic fibers or pretreated cellulosic fibers treated with particle binders and/or densification/softness aids known in the art can also be employed in accordance with the present invention. The particle binders serve to attach other materials, such as superabsorbent polymers, to the cellulosic fibers. Cellulosic fibers treated with suitable particle binders and/or densification/softness aids and the process for combining them with cellulose fibers are disclosed in the following U.S. patents and patent applications: (1) U.S. Pat. No. 5,543,215, entitled "Polymeric Binders for Binding Particles to Fibers"; (2) U.S. Pat. No. 5,538,783, entitled "Non-Polymeric Organic Binders for Binding Particles to Fibers"; (3) U.S. Pat. No. 5,300,192, entitled "Wet Laid Fiber Sheet Manufacturing With Reactivatable Binders for Binding Particles to Binders;" (4) U.S. Pat. No. 5,352,480, entitled "Method for Binding Particle to Fibers Using Reactivatable Binders"; (5) U.S. Pat. No. 5,308,896, entitled "Particle Binders for High-Bulk Fibers"; (6) U.S. Ser. No. 07/931,279, now U.S. Pat. No. 5,589,256, filed Aug. 17, 1992, entitled "Particle Binders that Enhance Fiber Densification"; (7) U.S. Ser. No. 08/107,469, now U.S. Pat. No. 5,672,418, filed Aug. 17, 1993, entitled "Particle Binders"; (8) U.S. Ser. No. 08/108,219, now U.S. Pat. No. 5,607,759, filed Aug. 17, 1993, entitled "Particle Binding to Fibers"; (9) U.S. Ser. No. 08/107,467, now U.S. Pat. No. 5,693,411, filed Aug. 17, 1993, entitled "Binders for Binding Water Soluble Particles to Fibers"; (10) U.S. Pat. No. 5,547,745, entitled "Particle Binders"; (11) U.S. Ser. No. 08/108,218, now U.S. Pat. No. 5,641,561, filed Aug. 17, 1993, entitled "Particle Binding to Fibers"; and (12) U.S. Pat. No. 5,308,896, entitled "Particle Binders for High-Bulk Fibers," all expressly incorporated herein by reference. One example of a suitable densification/softness aid is a mixture of 70% sorbitol and 30% glycerin. The absorbent is treated with sorbitol and glycerin by spraying the absorbent with the mixture or passing the absorbent through a curtain coater, or other means of adding a liquid to a absorbent sheet familiar to those skilled in the art.

Materials that enhance absorbent capacity, such as superabsorbent polymers, can also be combined with the unitary stratified composite of the present invention. A superabsorbent polymer as used herein is a polymeric material that is capable of absorbing large quantities of fluid by swelling and forming a hydrated gel (hydrogel). The superabsorbent polymers also can retain significant amounts of water under moderate pressures. Superabsorbent polymers generally fall into three classes, namely, starch graft copolymers, crosslinked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified crosslinked polyvinyl alcohol, a neutralized self-crosslinking polyacrylic acid, a crosslinked polyacrylate salt, carboxylated cellulose, and a neutralized crosslinked isobutylene-maleic anhydride copolymer. The superabsorbent polymers can be combined with the cellulosic fibers in amounts up to 70% by weight based on the total weight of fibers and polymer.

Superabsorbent polymers are available commercially, for example, starch graft polyacrylate hydrogel fines from Hoechst Celanese of Portsmouth, Va. These superabsorbent polymers come in a variety of sizes, morphologies, and absorbent properties. These are available from Hoechst Celanese under trade designations such as IM 1000 and IM 3500. Other superabsorbent particles are marketed under the trademarks SANWET (supplied by Sanyo Kasei Kogyo Kabushiki Kaisha), SUMIKA GEL (supplied by Sumitomo Kagaku Kabushiki Kaisha), which is suspension polymerized and spherical, as opposed to solution polymerized ground particles, FAVOR (supplied by Stockhausen of Greensboro, N.C.), and NORSOCRYL (supplied by Atochem). Other superabsorbent polymers are described in U.S. Pat. Nos. 4,160,059; 4,676,784; 4,673,402; 5,002,814; 5,057,166; 4,102,340; and 4,818,598, expressly incorporated herein by reference. Products such as diapers that incorporate superabsorbent polymers are shown in U.S. Pat. Nos. 3,669,103 and 3,670,731.

Increased wet and dry strength of the unitary stratified composite of the present invention can be accomplished with a binder. As used herein, the term "binder" refers to a system that is effective in mechanically intertwining or bonding the materials within the first stratum, the materials within the second stratum, and the first stratum to the second stratum. In one embodiment of the present invention, both strata include a binder. In another embodiment, only the second stratum includes a binder, and in still another embodiment, only the first stratum includes a binder. Suitable binders can include, but are not limited to, bonding agents such as thermoplastic and thermosetting materials, soluble bonding mediums used in combination with solvents, and wet strength agents. Alternatively, integral commingling and intimate contact between the composite's strata can be achieved through mechanical processes including, for example, hydroentanglement, embossing, tenderizing, and needling processes, among others.

Bonding agents useful in the binder in accordance with the present invention are those materials that (a) are capable of being combined with and dispersed throughout a web of fibers, (b) when activated, are capable of coating or otherwise adhering to the fibers or forming a binding matrix, and (c) when deactivated, are capable of binding at least some of the fibers together. The use of bonding agents with cellulose fiber webs is disclosed in U.S. patent application Ser. No. 08/337,642, filed Nov. 10, 1994, entitled "Densified Cellulose Fiber Pads and Methods of Making the Same," expressly incorporated herein by reference.

Suitable bonding agents include thermoplastic materials that are activated by melting at temperatures above room temperature. When these materials are melted, they will coat at least portions of the cellulose fibers with which they are combined. When the thermoplastic bonding agents are deactivated by cooling to a temperature below their melt point, and preferably no lower than room temperature, the bonding agent will, upon solidifying from the melted state, cause the cellulose fibers to be bound in a matrix.

Thermoplastic materials are the preferred binders, and can be combined with the fibers in the form of particles, emulsions, or as fibers. Suitable fibers can include those made from thermoplastic polymers, cellulosic or other fibers coated with thermoplastic polymers, and multicomponent fibers in which at least one of the components of the fiber comprises a thermoplastic polymer. Single and multicomponent fibers are manufactured from polyester, polyethylene, polypropylene, and other conventional thermoplastic fiber materials. The same thermoplastics can be used in particulate or emulsion form. Many single-component fibers are readily commercially available. Suitable multicomponent fibers include Celbond® fibers available from Hoechst Celanese Company. A preferred crimped polymer-based binder fiber is Hoechst Celanese Copolyolefin Bicomponent fiber, commercially available under the tradename CELBOND® from Hoechst Celanese Corporation, type 255, lot 33865A, having a detex of about 3.3, a denier of about 3.0, and a fiber length of about 6.4 mm. Suitable coated fibers can include cellulose fibers coated with latex or other thermoplastics, as disclosed in U.S. Pat. No. 5,230,959, issued Jul. 27, 1993, to Young et al., and U.S. Pat. No. 5,064,689, issued Nov. 12, 1991, to Young et al. The thermoplastic fibers are preferably combined with the cellulose fibers before or during the forming process. When used in particulate or emulsion form, the thermoplastics can be combined with the cellulose fibers before, during, or after the forming process.

Other suitable thermoplastic bonding agents include ethylene vinyl alcohol, polyvinyl acetate, acrylics, polyvinyl acetate acrylate, polyvinyl dichloride, ethylene vinyl acetate, ethylene vinyl chloride, polyvinyl chloride, styrene, styrene acrylate, styrene butadiene, styrene acrylonitrile, butadiene acrylonitrile, acrylonitrile butadiene styrene, ethylene acrylic acid, urethanes, polycarbonate, polyphenylene oxide, and polyimides.

Thermosetting materials also serve as excellent bonding agents for the present invention. Typical thermosetting materials are activated by heating to elevated temperatures at which crosslinking occurs. Alternatively, a resin can be activated by combining it with a suitable crosslinking catalyst before or after it has been applied to the cellulosic fiber. Thermosetting resins can be deactivated by allowing the crosslinking process to run to completion or by cooling to room temperature, at which point crosslinking ceases. When crosslinked, it is believed that the thermosetting materials form a matrix to bond the cellulose fibers. It is contemplated that other types of bonding agents can also be employed, for example, those that are activated by contact with steam, moisture, microwave energy, and other conventional means of activation.

Thermosetting bonding agents suitable for the present invention include phenolic resins, polyvinyl acetates, urea formaldehyde, melamine formaldehyde, and acrylics. Other thermosetting bonding agents include epoxy, phenolic, bismaleimide, polyimide, melamine formaldehyde, polyester, urethanes, and urea.

These bonding agents are normally combined with the fibers in the form of an aqueous emulsion. They can be combined with the fibers during the laying process. Alternatively, they can be sprayed onto a loose web after it has been formed.

As noted above, the binder utilized in accordance with the present invention can also be a soluble bonding medium that can be incorporated with the pulped cellulosic fibers, either in fiber form, or as particles or granules. If desired, the bonding medium can also be coated onto solvent insoluble fibers, such as cellulosic fibers, which can then be distributed throughout the matrix of fibers making up each of the strata of the present invention. It is presently preferred that the bonding medium comprise a fiber and be mixed with the components of each stratum prior to the formation of the absorbent. The use of soluble bonding mediums with cellulose fiber webs is disclosed in U. S. patent application Ser. No. 08/669,406, now U.S. Pat. No. 5,837,627, filed Jul. 3, 1996, entitled "Fibrous Web Having Improved Strength and Method of Making the Same," expressly incorporated herein by reference.

The solvents employed in accordance with the present invention must of course be capable of partially solubilizing the bonding medium as described above. The solvents must be able to partially dissipate or migrate from the surface of the bonding medium to allow the bonding medium to resolidify after partial solubilization. Nonvolatile solvents may be dissipated in most part by absorption into the bonding medium. It is preferred that the solvent be of limited volatility, so that little or no solvent will be lost to the atmosphere. By limited volatility it is meant that the solvent has a vapor pressure of 29 kPa or less at 25° C. Using a solvent of limited volatility may mitigate precautions usually necessary to control volatiles, and reduces the amount of solvent required to partially solubilize the bonding medium. In addition, use of solvents of limited volatility may eliminate the attendant processing problems encountered with volatile solvents, many of which are flammable and must be handled with care. The use of solvents of limited volatility may also reduce environmental problems. Furthermore, it is desirable for solvents to be nontoxic and capable of being dissipated from the surface of the bonding medium without adversely affecting the overall strength of the bonding medium.

Preferred bonding mediums and solvents of limited volatility are listed in the table set forth below.

| Bonding Medium | Solvent |
| --- | --- |
| cellulose acetate | triacetin |
|  | propane diol diacetate |
|  | propane diol dipropionate |
|  | propane diol dibutyrate |
|  | triethyl citrate |
|  | dimethyl phthalate |
|  | dibutyl phthalate |
| cellulose nitrate | triacetin |
| cellulose butyrate | triacetin |
| vinyl chloride/vinyl acetate copolymer | triacetin |
| cellulose fibers coated with polyvinyl acetate | triacetin |

Of the several bonding mediums listed, cellulose acetate is the most preferred. During manufacture of cellulose acetate fibers, a finish is usually applied to the fibers. Many times this finish is in the form of an oil. The presence of the finish sometimes detracts from the performance of a bonding medium. The presence of a finish may adversely affect the development as well as the strength of the bonds. It has been found that, when the bonding fibers are as straight as possible, as opposed to curled or kinked, they provide more contact points with the cellulosic fibers, and thus the final web will develop better strength. Similarly, when the bonding fibers are as long as is reasonably possible, the strength of the final web is increased. In addition to the foregoing, cellulose ethers and other cellulose esters may also be used as bonding medium. Acetylated pulp fibers may also be used as bonding medium and may be substituted with any number of acetyl groups. A preferred degree of substitution (D.S.) would be 2 to 3, and a most preferred D.S. would be 2.4.

The solvents used in combination with the bonding medium can be added in varying amounts. Strength is adversely affected if too little or too much solvent is added. At a cellulose acetate/pulp weight ratio of 10:90, it has been found that the solvents, and particularly triacetin, provide good strength when added in amounts ranging from 6% to 17%, and most preferably in the range of 9% to 14%, based on the weight of pulp fiber present.

The preferred forms of the solvents propane diol diacetate, dipropionate, and dibutyrate are the 1, 2 and 1, 3 forms. Other suitable solvents that work in accordance with present invention are butyl phthalyl butyl glycolate, N-cyclohexyl-p-toluenesulfonamide, diamyl phthalate, dibutyl phthalate, dibutyl succinate, dibutyl tartrate, diethylene glycol dipropionate, di-(2-ethoxyethyl)adipate, di-(2-ethoxyethyl)phthalate, diethyl adipate, diethyl phthalate, diethyl succinate, diethyl tartrate, di-(2-methoxyethyl)adipate, di-(2-methoxyethyl)phthalate, dimethyl phthalate, dipropyl phthalate, ethyl o-benzoylbenzoate, ethyl phthalyl ethyl glycolate, ethylene glycol diacetate, ethylene glycol dibutyrate, ethylene glycol dipropionate, methyl o-benzoylbenzoate, methyl phthalyl ethyl glycolate, N-o and p-totylethylsulfonamide, o-tolyl p-toluenesulfonate, tributyl citrate, tributyl phosphate, tributyrin, triethylene glycol diacetate, triethylene glycol dibutyrate, triethylene glycol dipropionate, and tripropionin.

The binder useful in the absorbent composite of the invention can also include polymeric agents that can coat or impregnate cellulosic fibers. Suitable such agents include cationic modified starch having nitrogen-containing groups (e.g., amino groups) such as those available from National Starch and Chemical Corp., Bridgewater, N.J.; latex; wet strength agents such as polyamide-epichlorohydrin resin (e.g., Kymene™ 557H, Hercules, Inc., Wilmington, Del.), polyacrylamide resin (described, for example, in U.S. Pat. No. 3,556,932 issued Jan. 19, 1971 to Coscia et al.; also, for example, the commercially available polyacrylamide marketed by American Cyanamid Co., Stanford, Conn., under the trade name Parez™ 631 NC); urea formaldehyde and melamine formaldehyde resins, and polyethylenimine resins. A general discussion on wet strength agents utilized in the paper field, and generally applicable in the present invention, can be found in TAPPI monograph series No. 29, "Wet Strength in Paper and Paperboard", Technical Association of the Pulp and Paper Industry (New York, 1965). Other binders could also include the use of scrim and/or continuous fiber filaments. For embodiments of the unitary stratified composite that include a wet strength agent as a binder, the wet strength agent is present in the composite in an amount from about 0.1% to about 2.0%, preferably from about 0.5% to about 1.0%, by weight of the total composite.

Additives can also be incorporated into a unitary stratified composite formed in accordance with the present invention during absorbent formation. The advantage of incorporating the additives during the absorbent formation is that they will also be attached to the absorbent matrix by certain of the solvents and bound in the matrix by the bonding medium. This provides a significant advantage in that the additives can be dispersed and retained throughout the matrix where desired. For example, the additives may be evenly dispersed and retained throughout the matrix. Additives that can be incorporated into the matrix include absorbent capacity enhancing materials such as superabsorbent polymers, adsorbents such as clays, zeolites, and activated carbon, brighteners such as titanium oxide, and odor absorbents such as sodium bicarbonate. Solvents can also reduce the dusting caused by the additives or the pulp itself because more of the fines are attached and bound to the matrix by the bonding medium.

In another aspect, the present invention provides methods for producing a unitary stratified composite. Generally, the unitary stratified composite is formed by forming a first stratum (as described above) on a second stratum (as described above), or the reverse. Intimate connection of the first stratum to the second stratum, and the formation of the transition zone, occurs when the two strata are laid down as described below. The unitary stratified composite of the present invention may be formed by an air-laid process, a wet-laid process, or a foam-formed process. A unitary stratified composite can be produced in accordance with the present invention in a variety of methods including, for example, air-laid or wet-laid web forming techniques known to those of ordinary skill in the pulp processing art. Representative examples of air-laid and wet-laid processes are disclosed in U.S. patent applications: Ser. No. 08/337,642, filed Nov. 10, 1994, entitled "Densified Cellulose Fiber Pads and Methods of Making the Same," and Ser. No. 08/669,406, filed Jul. 3, 1996, entitled "Fibrous Web Having Improved Strength and Method of Making the Same," both expressly incorporated herein by reference. The absorbent can also be produced by foam processes known in the art. See, for example, U.S. Pat. Nos. 3,716,449; 3,839,142; 3,871,952; 3,937,273; 3,938,782; 3,947,315; 4,166,090; 4,257,754; and 5,215,627, assigned to Wiggins Teape and related to the formation of fibrous materials from foamed aqueous fiber suspensions, expressly incorporated herein by reference. Generally, the methods for forming the unitary stratified composite of this invention include the sequential or simultaneous laying down of a first stratum (e.g., the components of the second stratum) followed by the laying down of a second stratum (e.g., the components of the first stratum) on the first laid stratum. The strata can also be laid in reverse order. The formed strata are then subjected to conditions sufficient to effect bonding (i.e., air drying and heating) between and within the strata to provide the unitary stratified composite of the invention. The processed web can be delivered in roll form, spooled form, or otherwise. Preferably, the method includes festooning as a finishing step.

Generally, the method for forming the unitary stratified composite includes combining the components of the first stratum, hydrophobic fibers and binder; combining the components of the second stratum, hydrophilic fibers and binder; and depositing the respective fibrous mixtures onto a foraminous support (e.g., a forming wire), either simultaneously or sequentially, such that intimate commingling between the fibers of the strata is achieved and the transition zone is formed. The combined deposited strata are then subjected to conditions sufficient to effect interfiber bonding (e.g., heating to effect thermal bonding) to provide the unitary stratified-composite of this invention.

For wet-laid and foam methods, the fiber/binder mixtures are aqueous or foam fibrous slurries. In these methods, the deposited slurries form a water- or foam-containing composite. Accordingly, these methods further include the step of removing at least a portion of water or foam from the wet composite on the foraminous support. The resulting wet stratified composite is then subjected to conditions, for example, heating, to effect drying and thermal bonding of the fibers and formation of the unitary stratified composite. For foam processes, the aqueous or foam slurry further includes a surfactant.

In the composite forming methods, intimate strata commingling and transition zone formation result from the deposition of the components from one strata onto the components of the other. The deposition process involves the laying down of fibrous streams, which correspond to the first and second strata, onto a foraminous support. Turbulence accompanies the deposition of the streams and mixing of the streams' components occurs. The mixing of components ultimately results in the formation of the composite's transition zone. For wet-laid and foam processes, the turbulence and fibrous component mixing is enhanced through the application of vacuum to the foraminous support, which serves to remove water from the deposited aqueous or foam fibrous slurries. The application of vacuum to the deposited strata during the drying process further increases the commingling of the strata and enhances the transition zone.

The fibrous slurries can be deposited onto the foraminous support through the use of a divided headbox, for example, a twin slice headbox, which deposits the slurries onto the support. Mixing of the two fibrous slurries is greatest when the components of the individual strata are deposited simultaneously. Alternatively, the fibrous slurries can be deposited onto the support sequentially through the use of offset headboxes. For methods that use offset headboxes, some settling of the components of the first laid stratum deposited on the support occurs prior to the deposition of the components of the second stratum.

Preferably, the unitary stratified composite of the present invention is prepared by a wet-laid or foam-formed process. For fabrication, the unitary stratified composite is preferably formed by a foam process, preferably a process by Ahlstrom Company (Helsinki, Finland). This process encompasses desirable manufacturing efficiencies while producing a product with desirable performance characteristics. The formation of a representative unitary stratified composite of the present invention by representative wet laid, air laid, foam, and commercial processes are described in Examples 1 through 4, respectively. The performance characteristics of representative unitary stratified composites produced by the methods noted above are described in Examples 6 through 8.

Figure 2:
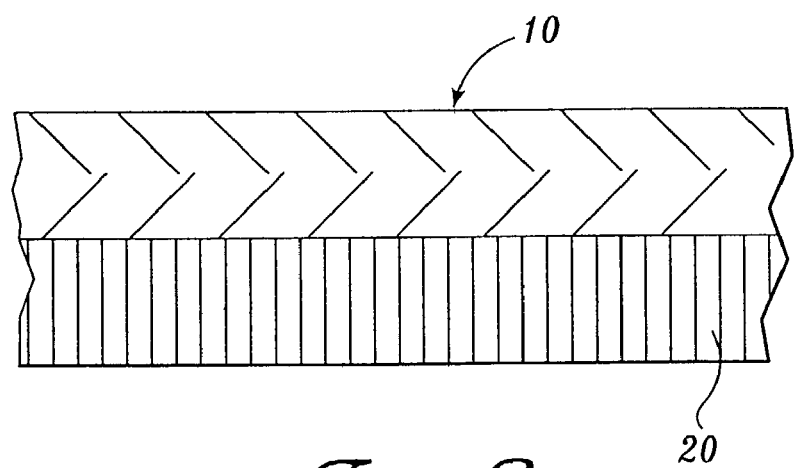
FIG. 2 is a schematic view of one absorbent article incorporating a unitary stratified composite produced in accordance with the present invention.
Figure 3:
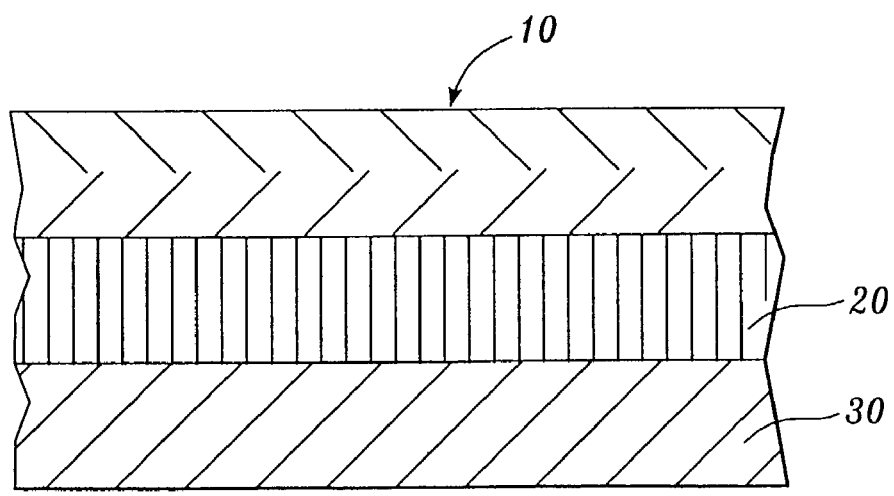
FIG. 3 is a schematic view of another absorbent article incorporating a unitary stratified composite produced in accordance with the present invention.
Figure 4:
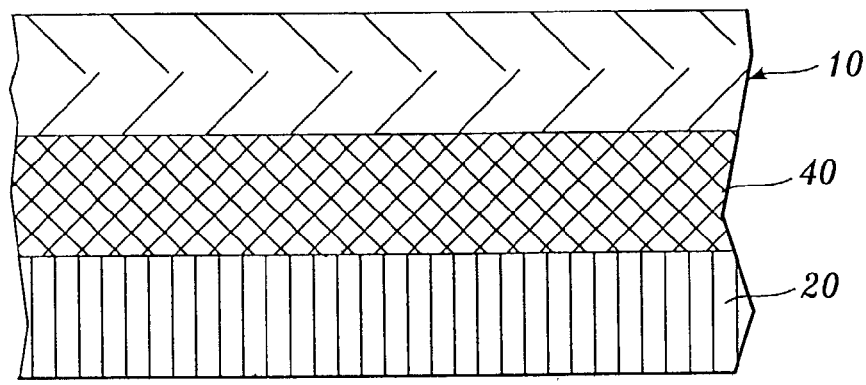
FIG. 4 is a schematic view of another absorbent article incorporating a unitary stratified composite produced in accordance with the present invention.

As noted above, the unitary stratified composite 10 of the present invention includes a first stratum 12 and a second stratum 14 as schematically depicted in FIG. 1. The absorbent composite can be incorporated in an absorbent article as the absorbent stratum. The absorbent composite can be used alone or, as illustrated in FIG. 2, can be used in combination with one or more secondary strata. In FIG. 2, the absorbent composite is employed as an upper acquisition/distribution stratum in combination with a storage stratum 20 composed of, for example, a fibrous web. Storage stratum 20, if desired, can also comprise a densified stratum of bonded cellulose fibers. As illustrated in FIG. 3, a third stratum 30 (e.g., a core or retention stratum) can also be employed, if desired, with a storage stratum 20 and absorbent 10. If desired, the retention stratum 30 can also be composed of a fibrous web such as, for example, densified bonded cellulose fibers. Alternatively, a distribution stratum 40 can be interposed between absorbent 10 and storage stratum 20 as illustrated in FIG. 4. Distribution stratum 40 is generally a hydrophilic fibrous material that includes, for example, hydrophilic fibers such as cellulosic fibers, preferably crosslinked cellulosic fibers, and a binder. In one preferred embodiment, the cellulosic fibers are crosslinked eucalyptus fibers. Distribution stratum 40 can optionally include superabsorbent polymeric material.

A variety of suitable constructs can be produced from the unitary stratified composite. The most common include absorptive consumer products such as diapers, feminine hygiene products such as feminine napkins, and adult incontinence products. For example, referring to FIG. 5, an absorbent article 50 comprises absorbent composite 10 and an underlying storage stratum 20. A liquid pervious facing sheet 16 overlies absorbent composite 10 and a liquid impervious backing sheet 18 underlies the storage stratum 20. The unitary stratified composite will provide advantageous liquid acquisition performance for use in, for example, diapers. The capillary structure of the absorbent composite will aid in fluid transport in multiple wettings. Generally, the storage stratum 20 includes a fibrous web, for example, a strengthened web of cellulose fibers, and may also incorporate additives, such as superabsorbent polymers to significantly increase the absorbent capacity of the storage stratum 20.

Figure 5:
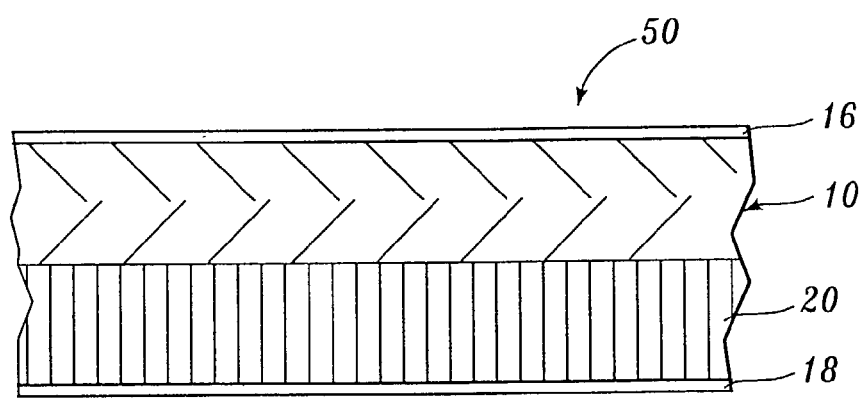
FIG. 5 is a schematic view of still another absorbent article incorporating a unitary stratified composite produced in accordance with the present invention.

The article of FIG. 5 can be assembled so that absorbent composite 10 is brought into contact with the storage stratum 20 while the binder in the latter is still active. Such a procedure will allow the storage stratum to bond to at least the lower surface of absorbent 10, and thus eliminate the need to use hot-melt glues to bond adjacent strata.

A stronger bond between absorbent composite 10 and the storage stratum 20 can be achieved by contacting the absorbent composite with the storage stratum while the absorbent composite's binder is still active. Similarly, laying the storage stratum 20 on the backing sheet 18 while the binder of the storage stratum is still active results in the bonding of stratum 20 to the backing sheet 18. In a similar manner, absorbent composite 10 may be bonded to the facing sheet 16 by laying the facing sheet on absorbent composite 10 while the binder therein is still active. Interbonding between strata can enhance and further facilitate fluid transport across the stratum interface.

Figure 6:
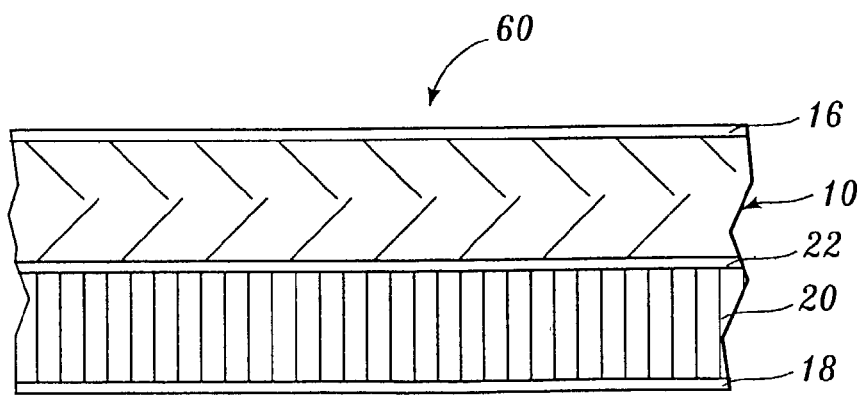
FIG. 6 is a schematic view of yet another absorbent article incorporating a unitary stratified composite produced in accordance with the present invention.

The construct in FIG. 5 is shown for purposes of exemplifying a typical absorbent article, such as a diaper or feminine napkin. One of ordinary skill will be able to make a variety of different absorbent constructs using the concepts taught herein. For example, a typical construction for an adult incontinence absorbent structure is shown in FIG. 6. The article 60 comprises a facing sheet 16, absorbent composite 10, a storage stratum 20, and a backing sheet 18. The facing sheet 16 is pervious to liquid while the backing sheet 18 is impervious to liquid. In this construct, a liquid pervious tissue 22 composed of a polar, fibrous material is positioned between absorbent composite 10 and storage stratum 20.

Figure 7:
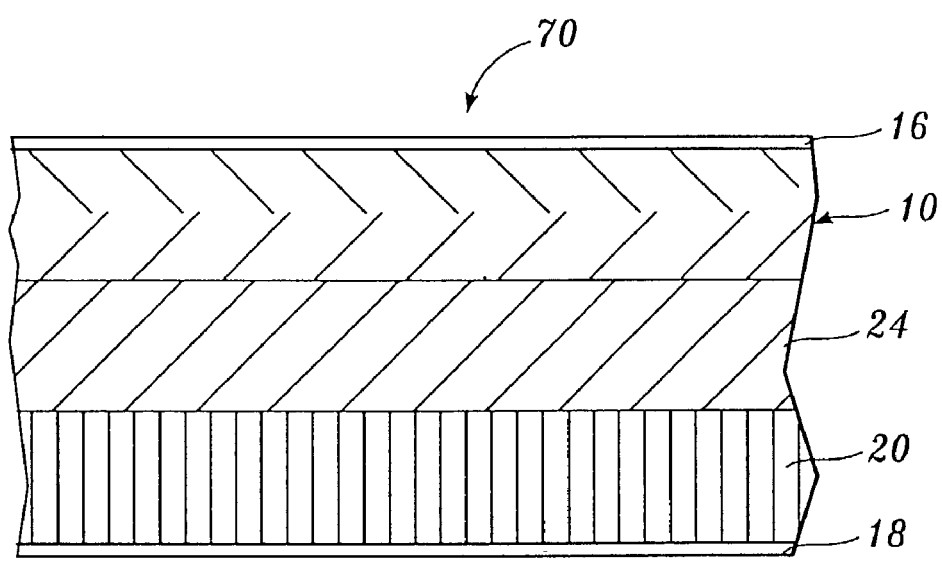
FIG. 7 is a schematic view of another absorbent article incorporating a unitary stratified composite produced in accordance with the present invention.

Referring to FIG. 7, another absorbent article 70 includes a backing sheet 18, a storage stratum 20, an intermediate stratum 24, an absorbent composite 10, and a facing sheet 16. The intermediate stratum 24 contains, for example, a densified fibrous material such as a combination of cellulose acetate and triacetin, which are combined just prior to forming the article. The intermediate stratum 24 can thus bond to both the absorbent composite 10 and the storage stratum 20 to form an absorbent article with much more integrity than one in which the absorbent composite and storage stratum are not bonded to each other. The hydrophilicity of stratum 24 can be adjusted in such a way as to create a hydrophilicity gradient among strata 10, 24, and 20. It should be understood that an independent intermediate stratum is not required in order to get stratum-to-stratum bonding. When one of two adjacent strata or both strata contain a binder, if the two strata are brought together when the bonding medium is still active; bonding between the two strata will occur and provide a stronger composite compared to a composite lacking any bonding. Alternatively, intermediate stratum 24 can be a distribution stratum as described above in reference to the construct of FIG. 4.

The unitary stratified composite of the present invention improves the surface dryness rewet performances, and acquisition rate of absorbent products and articles that incorporate the absorbent composite. The absorbent composite also provides increased pad integrity, improved appearance, and a reduction in wet collapse during use for absorbent products that incorporate the absorbent composite. Furthermore, because the unitary stratified composite can be manufactured and delivered in web form, absorbent product manufacturing processes that include the absorbent composite are simplified relative to manufacturing processes that involve the handling of bales of crosslinked fibers or fluff pulp. Thus, in addition to the increased performance provided to absorbent products that incorporate the absorbent composite of this invention, the absorbent composite offers economic advantages over the combination of separate strata of high-loft nonwoven fibers and crosslinked cellulose.

EXAMPLES

The following examples are provided for the purposes of illustration, and not limitation.

Example 1

Unitary Stratified Composite Formation: Wet Laid Method

This example illustrates a wet laid method for forming a representative unitary stratified composite of the present invention. In this example, the absorbent composite has a first stratum composed of 90% polyethylene terephthalate (fiber length 0.5 inches, 15 denier, crimped) (Hoechst Celanese Co.) and 10% Celbond® T-105 (Hoechst Celanese Co.), and a second stratum composed of a 90% crosslinked cellulose fiber (Weyerhaeuser Co.) and 10% Celbond® T-105.

Fiber Preparation

A lab size Waring blender was filled with 4 L of water and Celbond® T-105 (for the first stratum) was added. The mixture was blended for a short time to "open" the synthetic fibers. The polyethylene terephthalate (PET) fibers were then added to the Celbond® T-105/water mixture and blended for at least one minute to "open" the PET fibers and to effect mixing of the two synthetic fibers. The resulting aqueous mixture of fibers contained approximately 0.02 to 0.5% solids. After mixing, the aqueous fiber mixture was transferred to a secondary container.

A lab size Waring blender was filled with 4 L of water and Celbond® T-105 (for the second stratum) was added. The mixture was blended for a short time to "open" the synthetic fibers. The crosslinked cellulose fibers were then added to the Celbond® T-105/water mixture and blended for at least one minute to "open" the crosslinked cellulose fibers and to effect mixing of the two fibers. The resulting aqueous mixture of fibers contained approximately 0.07 to 1.0% solids. After mixing, the aqueous fiber mixture was transferred to a secondary container.

Sheet Formation

A sheet was prepared using a stratified sheet mold. To the mold filled with water was added the crosslinked cellulose fiber-Celbond® T-105 mixture prepared as described above. After thorough mixing in the mold, the mold was drained down to its baffles. The mold baffles were then closed, and the mold refilled with water. The baffles were reopened, and the mold drained again half way. The baffles were then closed and the mold refilled with water. A portion of the PET-Celbond® T-105 mixture prepared as described above was added to the top half of the mold. The contents of the top half of the mold were mixed, and then the mold was drained to the baffles. The baffles were then closed, and the top half of the mold refilled with water. Another portion of the PET-Celbond® T-105 mixture was then added to the mold and mixed. The baffles were again opened to drain the top half of the mold, refilled with water, and another portion of the PET-Celbond® T-105 mixture added with mixing. This procedure was repeated until all of the prepared PET-Celbond® T-105 mixture was added to the mold. Upon completion of the addition, the mold was finally drained and the resulting wet sheet carefully removed.

The representative unitary stratified composite was produced by placing the wet sheet in a through air dryer to dry and to effect bonding.

Example 2

Unitary Stratified Composite Formation: Air Laid Method

This example illustrates an air laid method for forming a representative unitary stratified composite of the present invention. In this example, the absorbent composite has a first stratum composed of 90% polyethylene terephthalate (fiber length 0.5 inches, 15 denier, crimped) (Hoechst Celanese) and 10% Celbond® T-105 (Hoechst Celanese), and a second stratum composed of a 90% crosslinked cellulose fiber (Weyerhaeuser Co.) and 10% Celbond® T-105.

Fiber Preparation

PET fibers and Celbond® T-105 for the first stratum were placed in a plastic bag and thoroughly mixed with an airstream. Crosslinked cellulose fibers and Celbond+T-105 for the bottom stratum were placed in a second plastic bag and mixed thoroughly with an airstream.

Sheet Formation

A pinmill was used to "open" the fibers. The resulting fibers were then evenly distributed on a tissue by first slowly metering the crosslinked cellulose fiber-Celbond® T-105 mixture into the air former, followed by slowly metering the PET fibers-Celbond® T-105 mixture into the air former on top of the stratum containing the crosslinked fibers.

The representative unitary stratified composite was produced by placing the resulting air sheet in a through air dryer to effect bonding.

Example 3

Unitary Stratified Composite Formation: Laboratory Foam Method

This example illustrates a laboratory foam method for forming a representative unitary stratified composite of the present invention. The absorbent composite has a first stratum composed of 90% polyethylene terephthalate (fiber length 0.5 inches, 15 denier, crimped) (Hoechst Celanese) and 10% Celbond® T-105 (Hoechst Celanese), and a second stratum composed of a 90% crosslinked cellulose fiber (Weyerhaeuser Co.) and 10% Celbond® T-105.

Fiber Preparation

The fibers were prepared as for the wet laid process described above in Example 1. The crosslinked cellulose fiber-Celbond® T-105 mixture was placed in a container and water added to form an aqueous mixture. The resulting mixture was then blended for a few seconds with an air-entrapping blade. A surfactant (Incronan 30, Croda, Inc.) was added to the blended mixture. Approximately 1 g active surfactant solids per gram fiber were added. The mixture was blended while slowly raising the mixer blade height with the rising foam. After about one minute, the mixing was terminated, and then restarted for another minute at constant mixer blade height. The resulting foam-fiber mixture has a volume of about three times the volume of the original water-fiber mixture.

A foam-fiber mixture was also prepared from the PET fiber-Celbond® T-105 mixture as described above for the crosslinked cellulose fiber-Celbond® T-105 mixture.

Sheet Formation

The crosslinked cellulose fiber-Celbond® T-105 foam-fiber mixture was rapidly poured into a sheet mold having an inclined diffusion plate. After the addition of the foam-fiber mixture, the plate was removed from the mold, and a strong vacuum was applied to reduce the foam-fiber height. The vacuum was discontinued and the diffusion plate replaced. The PET fiber-Celbond® T-105 foam-fiber mixture was then added to the sheet mold. The plate was removed and a strong vacuum was again applied to the mold. After the disappearance of most of the visible foam, the resulting sheet was removed from the mold and passed, along with a forming wire, over a slit couch to remove excess foam and water.

The representative unitary stratified composite was produced by placing the resulting damp sheet in a through air dryer to dry and to effect bonding.

Example 4

Unitary Stratified Composite Formation: Commercial Foam Method

This example illustrates a commercial foam method for forming a representative unitary stratified composite of the present invention. In this example, the absorbent composite has a first stratum composed of 90% polyethylene terephthalate (fiber length 0.5 inches, 15 denier, crimped) (Hoechst Celanese) and 10% Celbond® T-105 (Hoechst Celanese), and a second stratum composed of a 90% crosslinked cellulose fiber (Weyerhaeuser Co.) and 10% Celbond® T-105.

Fiber Preparation

Foam-fiber mixtures were prepared by combining dry fibers with surfactant and mixing for approximately 2 minutes with an air-entrapping blade. The crosslinked cellulose fiber-Celbond® fiber mixture was distributed into two tanks, and the PET-Celbond® fiber mixture was placed in a single tank.

Sheet Formation

Using transfer pumps, the foamy fiber slurries prepared as described above were pumped to an inclined multilayer headbox where the crosslinked cellulose fiber-Celbond® fiber mixture was first laid down followed by laying down of the PET-Celbond® fiber mixture. The wire was passed over two-slit couch vacuum.

The representative unitary stratified composite was produced by placing the resulting damp sheet in a through air dryer to dry and to effect bonding.

Example 5

Method for the Evaluation of Acquisition Time and Rewet for Representative Unitary Stratified Composites The performance characteristics of representative unitary stratified composites of the present invention were evaluated by incorporating the absorbent composite into a commercially available diaper and comparing the acquisition time and rewet relative to a control diaper. The acquisition time and rewet were determined in accordance with the multiple-dose rewet test described below.

Briefly, the multiple-dose rewet test measures the amount of synthetic urine released from an absorbent structure after each of three liquid applications, and the time required for each of the three liquid doses to wick into the product.

A preweighed sample of the absorbent structure is prepared for the test by determining the center of the structure's core, measuring 1 inch to the front for liquid application location, and marking with "X," and then placing a liquid application funnel (minimum 100 mL capacity, 5–7 mL/s flow rate) 4 inches above the surface of the sample. Commercially available diapers are used as controls, and these diapers incorporating the absorbent composite of the present invention were used for the comparative evaluation. Diapers incorporating the absorbent composite were prepared by cutting and inserting the absorbent composite into the diapers.

Once the sample was prepared, the test was conducted as follows. Flatten the sample, nonwoven side up, onto tabletop under the liquid application funnel. Fill funnel with dose (100 mL) of synthetic urine. Place dosing ring (5/32 inch stainless steel, 2 inch ID×3 inch height) onto the "X" measured on the samples. Apply first dose of synthetic urine within the dosing ring. Using a stopwatch, record the liquid acquisition time in seconds from the time the funnel valve is opened until the liquid wicks into the product from the bottom of the dosing ring. Wait twenty minutes. During the 20-minute waiting period after the first dose is applied, weigh a stack of filter papers (19–22 g, Whatman #3, 11.0 cm or equivalent, preexposed to room humidity for minimum of 2 hours before testing). During the second dose waiting period, take any dry filter papers left from first dose and add additional dry papers to total 29–32 g. During the third dose waiting period, take any dry papers and add additional dry papers to total 39–42 g. Place the stack of preweighed filter papers (i.e., dry blotter weight in Tables 1–9 below) on center of the wetted area and place cylindrical weight (8.9 cm diameter, 9.8 lb.) on top of these papers. Wait two minutes. Remove weight and weigh the papers. Record the weight change. Repeat the procedure two more times (i.e., for the second and third doses).

Rewet is reported as the amount of liquid absorbed back into the filter papers after each liquid dose (i.e., weight of wet filter papers—weight of dry filter papers).

Liquid acquisition time is reported as the length of time (seconds) necessary for the liquid to be absorbed into the product for each of the three doses.

The aqueous solution used in the tests is a synthetic urine available from National Scientific under the trade name RICCA. The synthetic urine is a saline solution containing 135 meq./l sodium, 8.6 meq./l calcium, 7.7 meq/l magnesium, 1.94% urea by weight (based on total weight), plus other ingredients.

Multiple-dose rewet test results for control diapers and diapers incorporating representative unitary stratified composites of the present invention are described in Examples 6 through 8.

Example 6

Evaluation of Acquisition Time and Rewet for Representative Unitary Stratified Composites: Denier Variation This example illustrates the effect that the variation in fiber denier in the first stratum of representative unitary stratified composites of the present invention has on the acquisition time and rewet of diapers incorporating the absorbent. Multiple-dose rewet tests were performed as described above in Example 5 for a commercially available diaper and diapers incorporating representative unitary stratified composites. The results are summarized in Tables 1 through 4 below. In Table 1, Control Diaper A refers to a whole diaper commercially available from Kimberly-Clark. In Tables 2–4, Test Diapers 1–3 refer to the Kimberly-Clark diaper incorporating representative unitary stratified composites having a first stratum composed of PET fibers having 1.5, 6, and 15 denier, respectively. The representative unitary stratified composites were produced by a wet laid method as described above in Example 1, and were formulated having a first stratum composed of 90% PET and 10% Celbond® and having a basis weight of about 22 g/m$^2$, and a second stratum composed of 90% crosslinked cellulose fibers and 10% Celbond® and having a basis weight of about 70 g/m$^2$.

Figure 8:
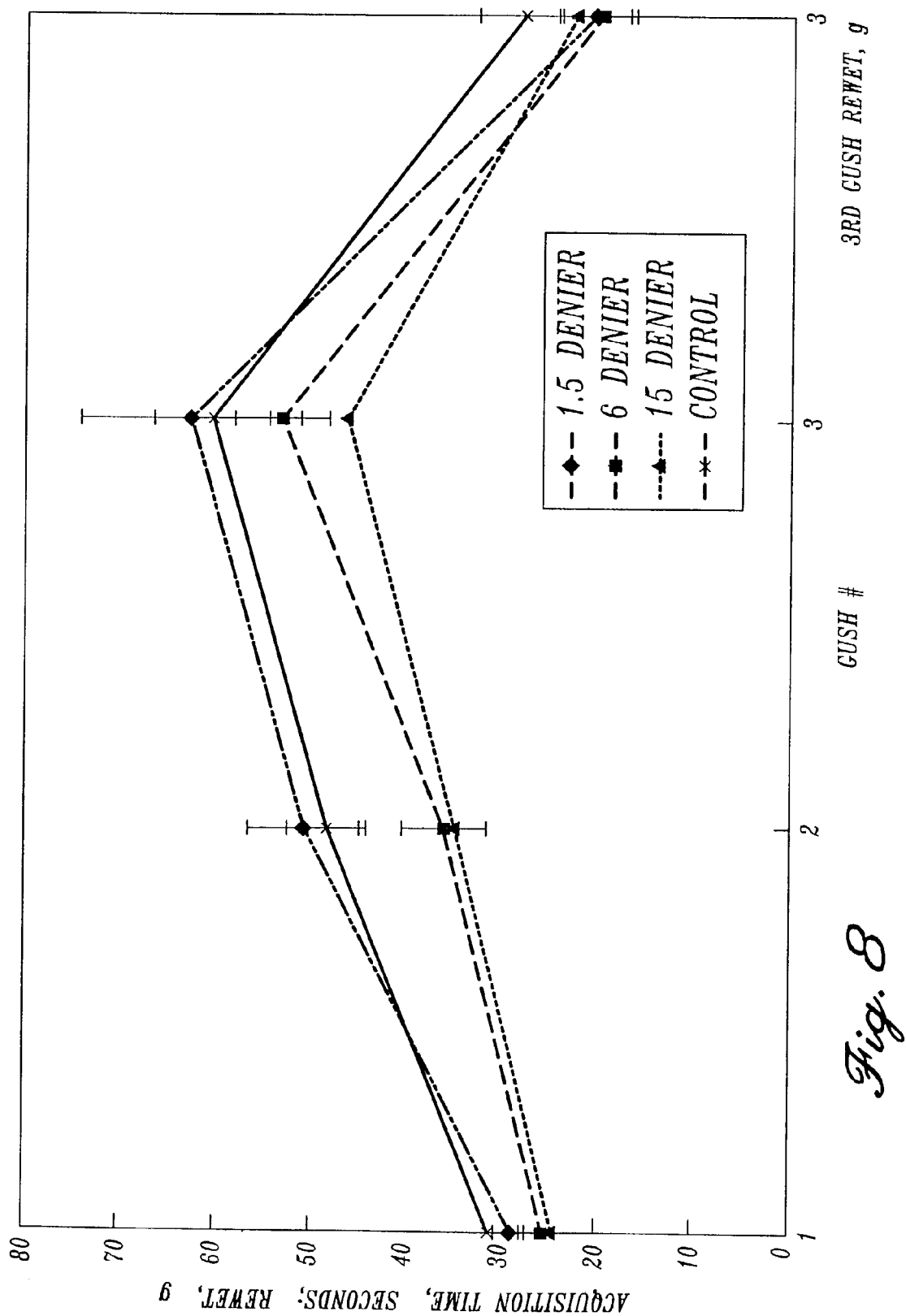
FIG. 8 is graph comparing the effect of first stratum fiber denier and pore size on the acquisition time and rewet performance of diapers incorporating representative unitary stratified composites produced in accordance with the present invention.

The results show that the diapers incorporating the absorbent composite provide significantly enhanced rewet performance and generally shorter acquisition times than the control diaper. The results also indicate that increased fiber denier in the first stratum of the absorbent composite increases the absorbent composite's performance characteristics. The results are graphically illustrated in FIG. 8.

TABLE 1

Multiple-Dose Rewet Test: Control Diaper A.

| SAMPLE NO | SAMPLE WEIGHT (grams) | | | Acquisition Time (seconds) | BLOTTER WT. (grams) | | |
|---|---|---|---|---|---|---|---|
| | | | | | dry | wet | wet-dry |
| 1 | 32.3 | 1st dose | | 33.87 | 20.7 | 20.8 | 0.1 |
| 2 | 34.8 | 1st dose | | 30.91 | 20.8 | 20.9 | 0.1 |
| 3 | 35.3 | 1st dose | | 26.47 | 20.8 | 20.9 | 0.1 |
| 4 | 34.9 | 1st dose | Average | 32.21 30.87 | 20.8 | 20.8 Average | 0 0.075 |
| | | | Std. Dev. | 3.17 | | Std. Avg. | 0.05 |
| 1 | | 2nd dose | | 52.90 | 30.7 | 34.0 | 3.3 |
| 2 | | 2nd dose | | 43.69 | 30.7 | 31.7 | 1.0 |

TABLE 1-continued

Multiple-Dose Rewet Test: Control Diaper A.

| SAMPLE NO | SAMPLE WEIGHT (grams) | | Acquisition Time (seconds) | BLOTTER WT. (grams) | | |
|---|---|---|---|---|---|---|
| | | | | dry | wet | wet-dry |
| 3 | | 2nd dose | 45.91 | 30.6 | 32.3 | 1.7 |
| 4 | | 2nd dose | 50.44 | 29.5 | 30.6 | 1.1 |
| | | Average | 48.24 | | Average | 1.775 |
| | | Std. Dev. | 4.19 | | Std. Dev. | 1.08 |
| 1 | | 3rd dose | 69.03 | 40.4 | 74.3 | 33.9 |
| 2 | | 3rd dose | 58.09 | 40.5 | 63.2 | 22.7 |
| 3 | | 3rd dose | 54.81 | 40.5 | 70.6 | 30.1 |
| 4 | | 3rd dose | 60.72 | 40.5 | 86.0 | 25.5 |
| | | Average | 60.66 | | Average | 28.05 |
| | | Std. Dev. | 6.08 | | Std. Dev. | 4.95 |

TABLE 2

Multiple-Dose Rewet Test: Test Diaper 1.

| SAMPLE NO | SAMPLE WEIGHT (grams) | | Acquisition Time (seconds) | BLOTTER WT. (grams) | | |
|---|---|---|---|---|---|---|
| | | | | dry | wet | wet-dry |
| 1 | 34.1 | 1st dose | 30.81 | 20.6 | 20.7 | 0.1 |
| 2 | 34.9 | 1st dose | 29.18 | 20.4 | 20.5 | 0.1 |
| 3 | 34.6 | 1st dose | 27.25 | 21.0 | 21.0 | 0 |
| 4 | 35.2 | 1st dose | 27.63 | 20.7 | 20.7 | 0 |
| | | Average | 28.72 | | Average | 0.05 |
| | | Std. Dev. | 1.63 | | Std. Avg. | 0.06 |
| 1 | | 2nd dose | 59.09 | 29.5 | 29.6 | 0.1 |
| 2 | | 2nd dose | 50.41 | 30.9 | 31.2 | 0.3 |
| 3 | | 2nd dose | 46.06 | 30.6 | 32.3 | 1.7 |
| 4 | | 2nd dose | 47.16 | 30.7 | 30.8 | 0.1 |
| | | Average | 50.68 | | Average | 0.55 |
| | | Std. Dev. | 5.90 | | Std. Dev. | 0.77 |
| 1 | | 3rd dose | 63.84 | 39.3 | 65.2 | 25.9 |
| 2 | | 3rd dose | 58.97 | 40.5 | 58.2 | 17.7 |
| 3 | | 3rd dose | 50.56 | 39.8 | 60.6 | 20.8 |
| 4 | | 3rd dose | 78.25 | 40.7 | 58.3 | 17.6 |
| | | Average | 62.91 | | Average | 20.50 |
| | | Std. Dev. | 11.61 | | Std. Dev. | 3.89 |

TABLE 3

Multiple-Dose Rewet Test: Test Diaper 2.

| SAMPLE NO | SAMPLE WEIGHT (grams) | | Acquisition Time (seconds) | BLOTTER WT. (grams) | | |
|---|---|---|---|---|---|---|
| | | | | dry | wet | wet-dry |
| 1 | 34.8 | 1st dose | 25.91 | 20.4 | 20.4 | 0.0 |
| 2 | 35.5 | 1st dose | 25.87 | 20.6 | 20.7 | 0.1 |
| 3 | 34.1 | 1st dose | 26.90 | 20.2 | 20.2 | 0 |
| 4 | 33.2 | 1st dose | 22.53 | 20.8 | 20.9 | 0.1 |
| | | Average | 25.30 | | Average | 0.05 |
| | | Std. Dev. | 1.91 | | Std. Avg. | 0.06 |
| 1 | | 2nd dose | 41.13 | 31.0 | 31.3 | 0.3 |
| 2 | | 2nd dose | 30.31 | 30.4 | 30.7 | 0.3 |
| 3 | | 2nd dose | 36.25 | 30.2 | 31.9 | 1.7 |
| 4 | | 2nd dose | 35.69 | 30.5 | 40.3 | 9.8 |
| | | Average | 35.85 | | Average | 3.03 |
| | | Std. Dev. | 4.43 | | Std. Dev. | 4.56 |
| 1 | | 3rd dose | 53.68 | 40.7 | 60.2 | 19.5 |
| 2 | | 3rd dose | 46.07 | 40.7 | 59.6 | 18.9 |
| 3 | | 3rd dose | 57.28 | 39.8 | 63.3 | 23.5 |
| 4 | | 3rd dose | 56.03 | 39.3 | 56.8 | 17.5 |
| | | Average | 53.27 | | Average | 19.86 |
| | | Std. Dev. | 5.02 | | Std. Dev. | 2.57 |

TABLE 4

Multiple-Dose Rewet Test: Test Diaper 3.

| SAMPLE NO | SAMPLE WEIGHT (grams) | | Acquisition Time (seconds) | BLOTTER WT. (grams) | | |
|---|---|---|---|---|---|---|
| | | | | dry | wet | wet-dry |
| 1 | 34.0 | 1st dose | 25.03 | 20.6 | 20.7 | 0.1 |
| 2 | 34.7 | 1st dose | 23.44 | 20.5 | 20.5 | 0 |
| 3 | 33.1 | 1st dose | 23.75 | 20.4 | 20.5 | 0.1 |
| 4 | 35.0 | 1st dose | 24.15 | 20.6 | 20.7 | 0.1 |
| | | Average | 24.09 | | Average | 0.07 |
| | | Std. Dev. | 0.69 | | Std. Avg. | 0.05 |
| 1 | | 2nd dose | 36.16 | 30.6 | 40.8 | 10.2 |
| 2 | | 2nd dose | 31.16 | 30.7 | 37.2 | 6.5 |
| 3 | | 2nd dose | 36.41 | 31.0 | 39.9 | 8.9 |
| 4 | | 2nd dose | 35.40 | 30.7 | 34.3 | 3.6 |
| | | Average | 34.8 | | Average | 7.30 |
| | | Std. Dev. | 2.45 | | Std. Dev. | 2.90 |

TABLE 4-continued

Multiple-Dose Rewet Test: Test Diaper 3.

| SAMPLE NO | SAMPLE WEIGHT (grams) | | Acquisition Time (seconds) | BLOTTER WT. (grams) | | |
|---|---|---|---|---|---|---|
| | | | | dry | wet | wet-dry |
| 1 | | 3rd dose | 47.38 | 40.9 | 65.0 | 24.1 |
| 2 | | 3rd dose | 43.78 | 40.0 | 61.0 | 21 |
| 3 | | 3rd dose | 46.56 | 41.0 | 65.8 | 24.8 |
| 4 | | 3rd dose | 47.78 | 40.0 | 61.4 | 21.4 |
| | | Average | 46.38 | | Average | 22.83 |
| | | Std. Dev. | 1.80 | | Std. Dev. | 1.91 |

Example 7

Evaluation of Acquisition Time and Rewet for a Representative Unitary Stratified Composite: Binder Variation This example illustrates the effect that the variation in binder in representative unitary stratified composites of the present invention has on the acquisition time and rewet of diapers incorporating the absorbent. Multiple-dose rewet tests were performed as described above in Example 5 for a commercially available diaper and diapers incorporating representative unitary stratified composites. The results are summarized in Tables 5 and 6 below. The control diaper was the same as for Example 6 above, and its performance summarized in Table 1. In Table 5, Test Diaper 4 refers to the Kimberly-Clark diaper incorporating a representative unitary stratified composite having a first stratum composed of 90% PET fibers (15 denier, 0.5 inch length, crimped) and 10% cellulose acetate/triacetin treated fibers and having a basis weight of about 22 g/m$^2$, and having a second stratum composed of 90% crosslinked cellulose fibers and 10% cellulose acetate/triacetin (with 10% triacetin add-on) treated fibers and having a basis weight of about 70 g/m$^2$. In Table 6, Test Diaper 5 refers to the Kimberly-Clark diaper incorporating a representative unitary stratified composite having a first stratum composed of 90% PET fibers (15 denier, 0.5 inch length, crimped) and 10% Celbond® and having a basis weight of about 22 g/m$^2$, and having a second stratum composed of 90% crosslinked cellulose fibers and 10% Celbond® and having a basis weight of about 70 g/m$^2$. The representative unitary stratified composites were produced by a wet laid method as described above in Example 1.

Figure 9:
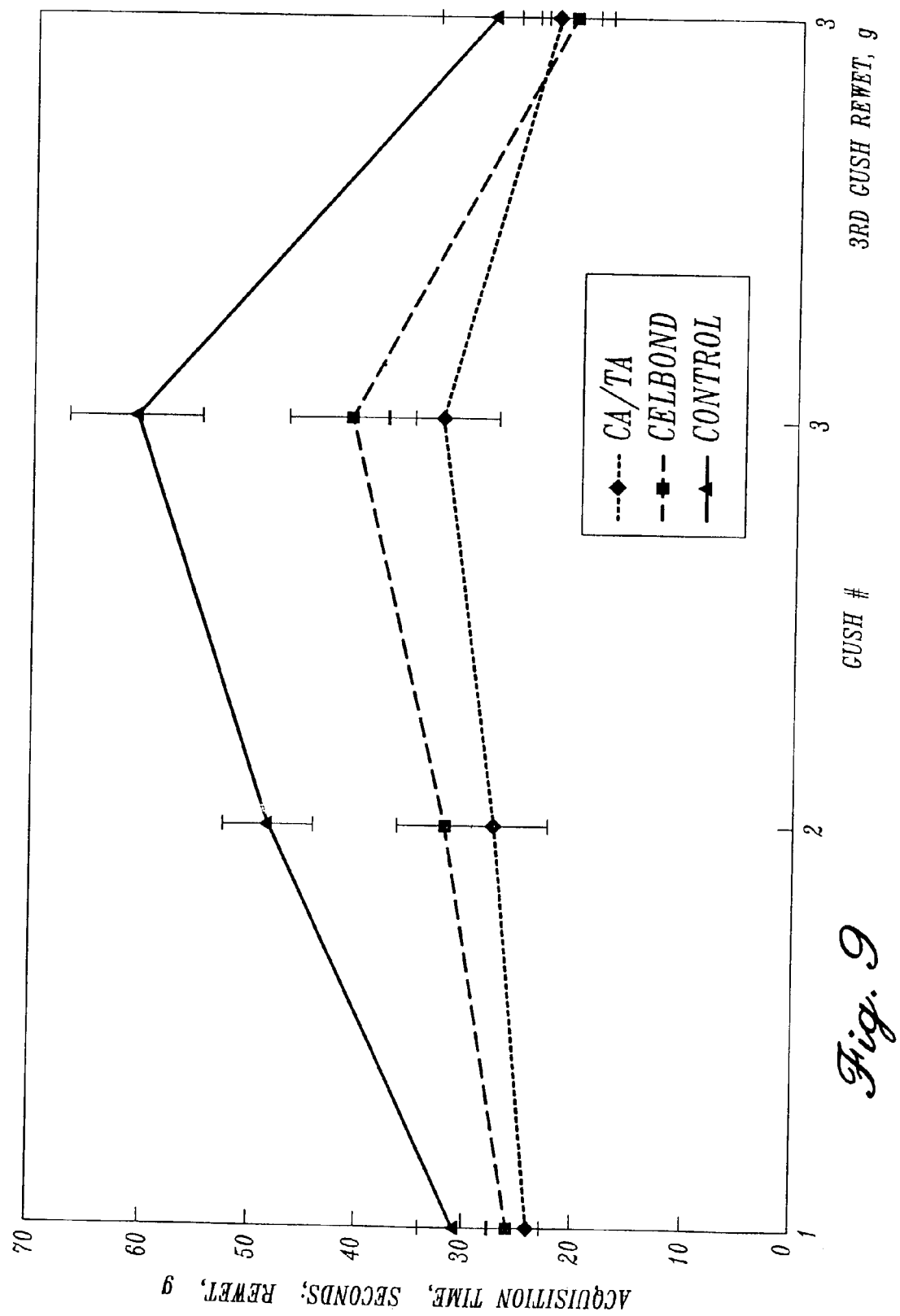
FIG. 9 is graph comparing the effect of a binder system on the acquisition time and rewet performance of diapers incorporating representative unitary stratified composites produced in accordance with the present invention.

The results show that the diapers incorporating the absorbent composite provide significantly enhanced rewet performance and generally shorter acquisition times than the control diaper. The results also indicate that the absorbent composite that includes cellulose acetate/triacetin treated fibers as the binder provides enhanced performance characteristics. The results are graphically illustrated in FIG. 9.

TABLE 5

Multiple-Dose Rewet Test: Test Diaper 4.

| SAMPLE NO | SAMPLE WEIGHT (grams) | | Acquisition Time (seconds) | BLOTTER WT. (grams) | | |
|---|---|---|---|---|---|---|
| | | | | dry | wet | wet-dry |
| 1 | 36.0 | 1st dose | 23.04 | 20.4 | 20.6 | 0.2 |
| 2 | 32.6 | 1st dose | 25.68 | 20.3 | 20.6 | 0.3 |
| 3 | 32.8 | 1st dose | 23.78 | 20.4 | 20.6 | 0.2 |
| 4 | 35.1 | 1st dose | 23.40 | 20.7 | 20.8 | 0.1 |
| | | Average | 23.98 | | Average | 0.20 |
| | | Std. Dev. | 1.18 | | Std. Avg. | 0.08 |
| 1 | | 2nd dose | 25.68 | 30.8 | 38.6 | 7.8 |
| 2 | | 2nd dose | 26.94 | 30.7 | 44.9 | 14.2 |
| 3 | | 2nd dose | 34.16 | 30.8 | 46.3 | 15.5 |
| 4 | | 2nd dose | 22.38 | 29.5 | 39.6 | 10.1 |
| | | Average | 27.29 | | Average | 11.9 |
| | | Std. Dev. | 4.97 | | Std. Dev. | 3.57 |
| 1 | | 3rd dose | 27.69 | 39.6 | 57.2 | 17.6 |
| 2 | | 3rd dose | 32.59 | 39.7 | 62.3 | 22.6 |
| 3 | | 3rd dose | 39.41 | 40.8 | 67.3 | 26.5 |
| 4 | | 3rd dose | 29.53 | 40.4 | 61.8 | 21.4 |
| | | Average | 32.31 | | Average | 22.03 |
| | | Std. Dev. | 5.15 | | Std. Dev. | 3.67 |

TABLE 6

Multiple-Dose Rewet Test: Test Diaper 5.

| SAMPLE NO | SAMPLE WEIGHT (grams) | | Acquisition Time (seconds) | BLOTTER WT. (grams) | | |
|---|---|---|---|---|---|---|
| | | | | dry | wet | wet-dry |
| 1 | 37.2 | 1st dose | 24.03 | 20.7 | 20.9 | 0.2 |
| 2 | 34.8 | 1st dose | 24.81 | 20.9 | 21.1 | 0.2 |
| 3 | 33.2 | 1st dose | 27.56 | 20.9 | 21.0 | 0.1 |
| 4 | 34.5 | 1st dose | 27.10 | 20.9 | 21.0 | 0.1 |
| | | Average | 25.88 | | Average | 0.15 |
| | | Std. Dev. | 1.72 | | Std. Avg | 0.06 |
| 1 | | 2nd dose | 25.46 | 30.8 | 34.3 | 3.5 |
| 2 | | 2nd dose | 32.94 | 30.7 | 43.2 | 12.5 |
| 3 | | 2nd dose | 33.22 | 30.7 | 44.3 | 13.6 |
| 4 | | 2nd dose | 35.81 | 30.9 | 40.8 | 9.9 |
| | | Average | 31.86 | | Average | 9.88 |
| | | Std. Dev. | 4.46 | | Std. Dev. | 4.52 |

TABLE 6-continued

Multiple-Dose Rewet Test: Test Diaper 5.

| SAMPLE NO | SAMPLE WEIGHT (grams) | | Acquisition Time (seconds) | BLOTTER WT. (grams) | | |
|---|---|---|---|---|---|---|
| | | | | dry | wet | wet-dry |
| 1 | | 3rd dose | 33.47 | 40.5 | 56.6 | 16 |
| 2 | | 3rd dose | 38.75 | 40.7 | 61.3 | 20.6 |
| 3 | | 3rd dose | 45.62 | 40.9 | 65.0 | 24.1 |
| 4 | | 3rd dose | 45.37 | 40.0 | 61.5 | 21.5 |
| | | Average | 40.80 | | Average | 20.56 |
| | | Std. Dev. | 5.83 | | Std. Dev. | 3.38 |

Example 8

Evaluation of Acquisition Time and Rewet for a Representative Unitary Stratified Composite: Densified and Undensified This example illustrates the effect that densification of a representative unitary stratified composite of the present invention has on the acquisition time and rewet of diapers incorporating the absorbent composite. Multiple-dose rewet tests were performed as described above in Example 5 for a commercially available diaper and diapers incorporating densified and undensified representative unitary stratified composites. The results are summarized in Tables 7–9 below. In Table 7, Control Diaper B refers to a whole diaper commercially available from Proctor and Gamble. In Tables 8 and 9, Test Diapers 6 and 7 refer to the Proctor and Gamble diaper incorporating representative undensified and densified unitary stratified composites, respectively. The representative unitary stratified composites were produced by a foam method as generally described above in Example 4, and were formulated having a first stratum composed of 80% PET fibers (15 denier, 0.5 inch length, crimped) and 20% Celbond® and having a basis weight of about 40 g/m², and a second stratum composed of 80% crosslinked cellulose fibers and 20% Celbond® and having a basis weight of about 110 g/m². The densified unitary stratified composite was prepared by cold calendering densification to 0.064 g/cm³. The undensified absorbent composite had a density of about 0.030 g/cm³.

Figure 10:
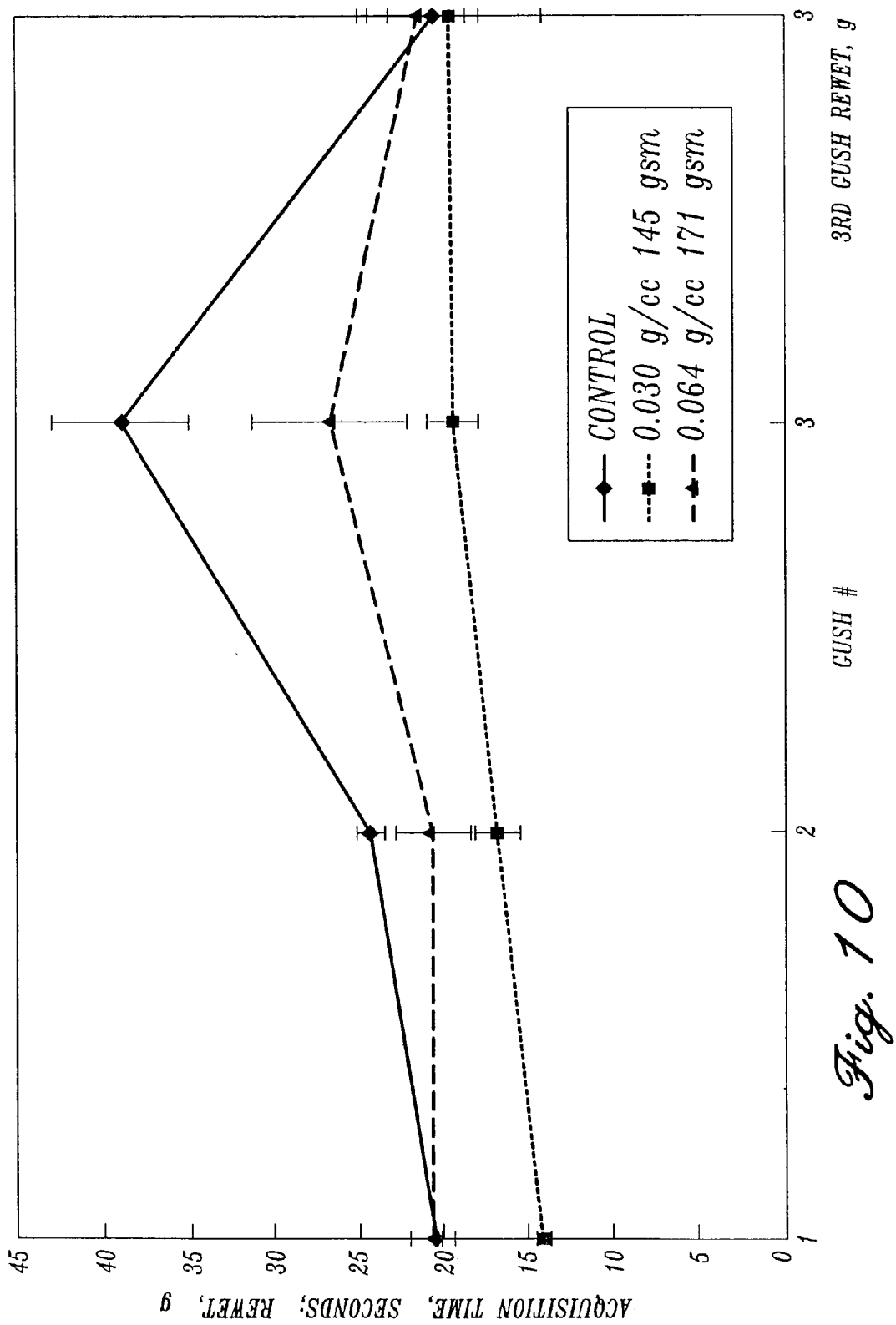
FIG. 10 is graph comparing the effect of densification on the acquisition time and rewet performance of diapers incorporating representative unitary stratified composites produced in accordance with the present invention.
Figure 11:
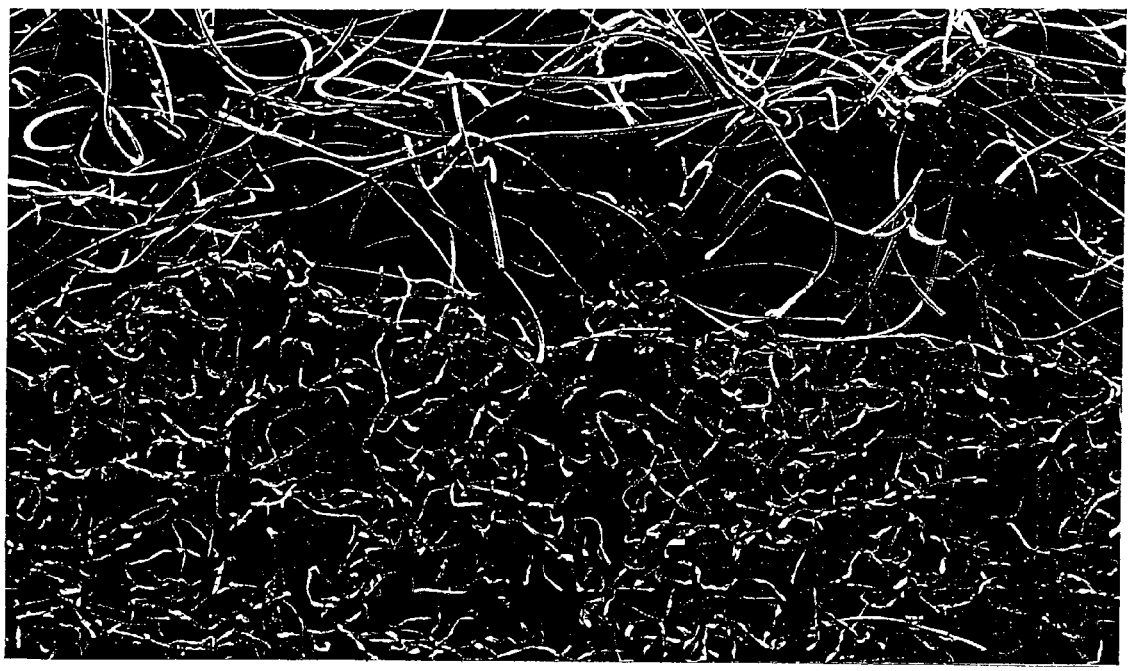
FIG. 11 is a photomicrograph (15.0×magnification) of a portion of a representative unitary stratified composite produced by an air-laid method in accordance with the present invention.
Figure 12:
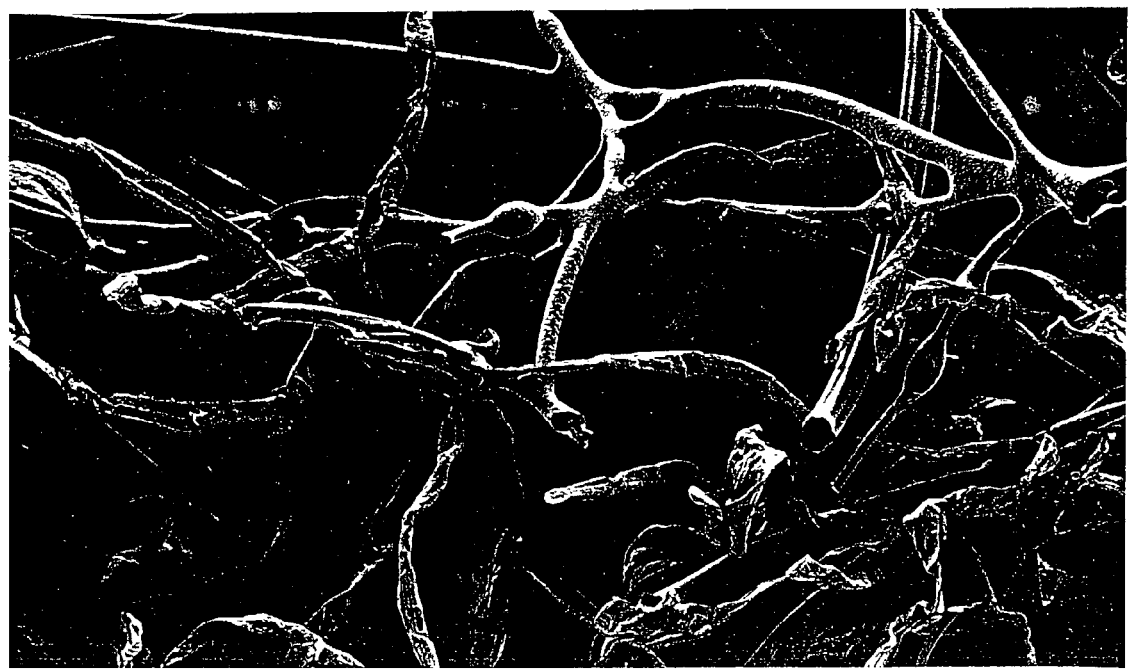
FIG. 12 is a photomicrograph (100×magnification) of a portion of the representative unitary stratified composite shown in FIG. 11.
Figure 13:
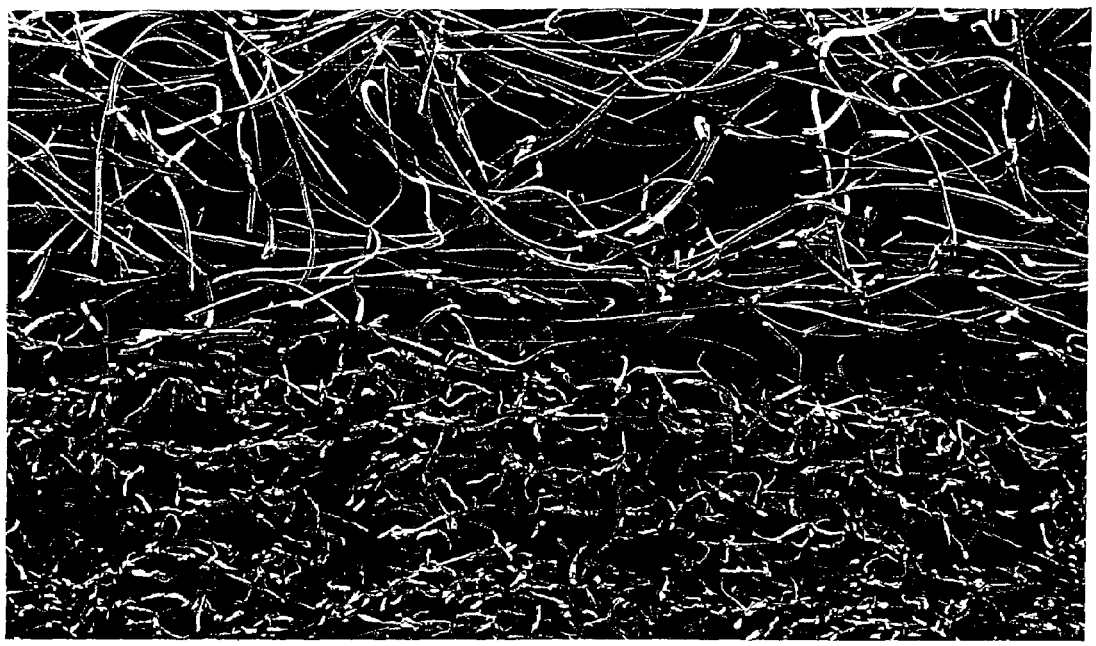
FIG. 13 is a photomicrograph (15×magnification) of a portion of a representative unitary stratified composite produced by a wet-laid method in accordance with the present invention.
Figure 14:
FIG. 14 is a photomicrograph (100×magnification) of a portion of the representative unitary stratified composite shown in FIG. 13.
Figure 15:
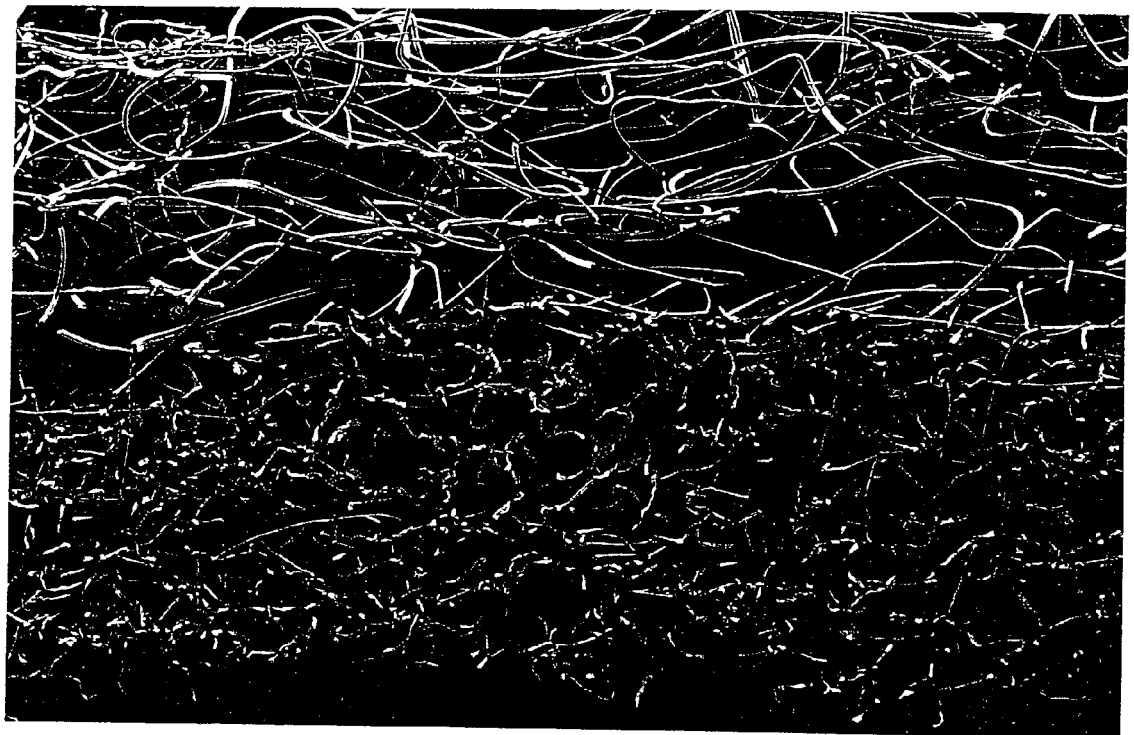
FIG. 15 is a photomicrograph (15×magnification) of a portion of a representative unitary stratified composite produced by a foam-formed method in accordance with the present invention.
Figure 16:
FIG. 16 is a photomicrograph (100×magnification) of a portion of the representative unitary stratified composite shown in FIG. 15.
Figure 17:
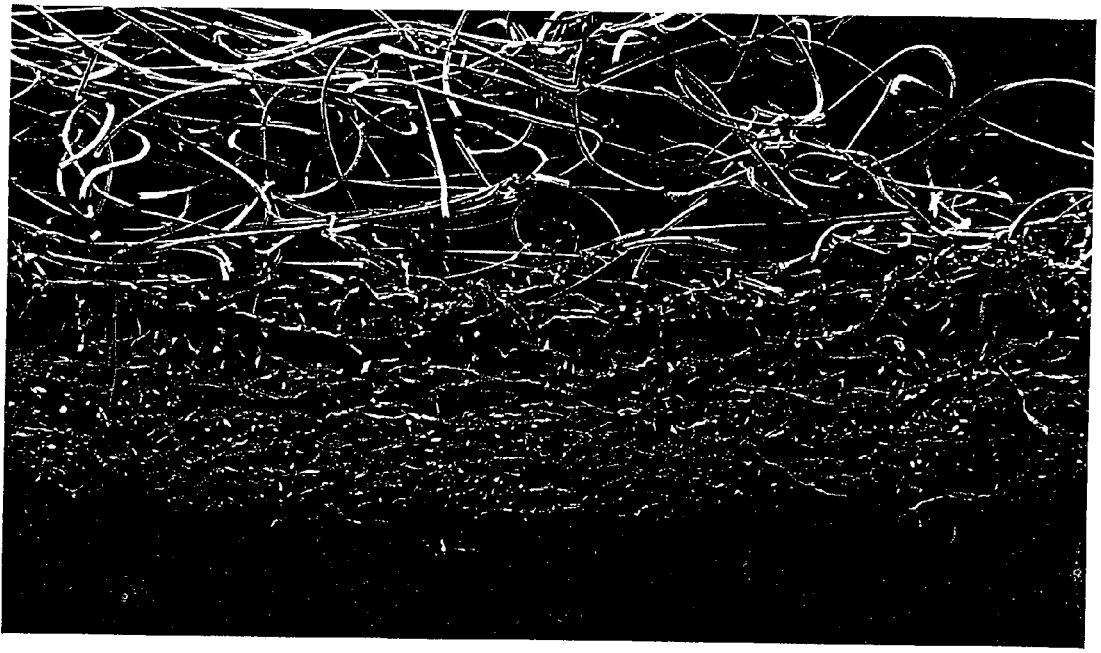
FIG. 17 is a photomicrograph (15×magnification) of a portion of a representative unitary stratified composite produced by a foam-formed method in accordance with the present invention.
Figure 18:
FIG. 18 is a photomicrograph (100×magnification) of a portion of the representative unitary stratified composite shown in FIG. 17.

The results show that the diapers incorporating the absorbent composite provide significantly enhanced rewet performance and generally shorter acquisition times than the control diaper. The results also indicate that undensified unitary stratified composite increases the absorbent composite's performance characteristics. The results are graphically illustrated in FIG. 10.

TABLE 7

Multiple-Dose Rewet Test: Control Diaper B.

| SAMPLE NO | SAMPLE WEIGHT (grams) | | Acquisition Time (seconds) | BLOTTER WT. (grams) | | |
|---|---|---|---|---|---|---|
| | | | | dry | wet | wet-dry |
| 1 | 48.0 | 1st dose | 20 | 20.86 | 20.95 | 0.09 |
| 2 | 48.0 | 1st dose | 21 | 20.11 | 20.21 | 0.1 |
| 3 | 48.0 | 1st dose | 21 | 20.32 | 20.42 | 0.1 |
| | | Average | 20 | | Average | 0.10 |
| | | Std. Dev. | 0 | | Std. Avg. | 0.01 |
| | | 2nd dose | 23 | 30.47 | 34.76 | 4.29 |
| | | 2nd dose | 25 | 30.52 | 36.01 | 5.49 |
| | | 2nd dose | 25 | 30.94 | 33.48 | 2.54 |
| | | Average | 24 | | Average | 4.11 |
| | | Std. Dev. | 1 | | Std. Dev. | 1.48 |
| | | 3rd dose | 44 | 40.84 | 61.02 | 20.18 |
| | | 3rd dose | 36 | 39.24 | 57.40 | 18.16 |
| | | 3rd dose | 37 | 39.27 | 62.83 | 23.56 |
| | | Average | 39 | | Average | 20.63 |
| | | Std. Dev. | 4 | | Std. Dev. | 2.73 |

TABLE 8

Multiple-Dose Rewet Test: Test Diaper 6.

| SAMPLE NO | SAMPLE WEIGHT (grams) | | Acquisition Time (seconds) | BLOTTER WT. (grams) | | |
|---|---|---|---|---|---|---|
| | | | | dry | wet | wet-dry |
| 1 | 45.6 | 1st dose | 14 | 20.66 | 21.17 | 0.51 |
| 2 | 45.6 | 1st dose | 15 | 19.18 | 19.65 | 0.47 |
| 3 | 45.6 | 1st dose | 14 | 19.14 | 19.72 | 0.58 |
| | | Average | 14 | | Average | 0.52 |
| | | Std. Dev. | 0 | | Std. Avg. | 0.06 |
| | | 2nd dose | 17 | 30.97 | 33.60 | 2.63 |
| | | 2nd dose | 15 | 29.27 | 30.54 | 1.27 |
| | | 2nd dose | 18 | 29.29 | 32.31 | 3.02 |
| | | Average | 17 | | Average | 2.31 |
| | | Std. Dev. | 1 | | Std. Dev. | 0.92 |
| | | 3rd dose | 21 | 39.43 | 60.28 | 20.85 |
| | | 3rd dose | 19 | 39.28 | 52.97 | 13.69 |
| | | 3rd dose | 18 | 39.82 | 64.31 | 24.49 |
| | | Average | 19 | | Average | 19.68 |
| | | Std. Dev. | 2 | | Std. Dev. | 5.49 |

TABLE 9

Multiple-Dose Rewet Test: Test Diaper 7.

| SAMPLE NO | SAMPLE WEIGHT (grams) | | Acquisition Time (seconds) | BLOTTER WT. (grams) | | |
|---|---|---|---|---|---|---|
| | | | | dry | wet | wet-dry |
| 1 | 46.0 | 1st dose | 19 | 19.04 | 19.18 | 0.14 |
| 2 | 46.0 | 1st dose | 21 | 20.39 | 20.76 | 0.37 |
| 3 | 46.0 | 1st dose | 22 | 20.54 | 20.91 | 0.37 |
| | | Average | 21 | | Average | 0.29 |
| | | Std. Dev. | 1 | | Std Avg. | 0.13 |
| | | 2nd dose | 21 | 29.19 | 31.92 | 2.73 |
| | | 2nd dose | 18 | 30.62 | 39.36 | 8.74 |
| | | 2nd dose | 23 | 29.23 | 33.15 | 3.92 |
| | | Average | 21 | | Average | 5.13 |
| | | Std. Dev. | 2 | | Std. Dev. | 3.18 |
| | | 3rd dose | 28 | 39.45 | 58.76 | 19.31 |
| | | 3rd dose | 22 | 39.64 | 60.36 | 20.72 |
| | | 3rd dose | 31 | 39.80 | 64.73 | 24.93 |
| | | Average | 27 | | Average | 21.65 |
| | | Std. Dev. | 5 | | Std. Dev. | 2.92 |

While the preferred embodiment of the invention has been illustrated and described, it will be appreciated that various changes can be made therein without departing from the spirit and scope of the invention.

The invention claimed is:

1. A method for forming an unitary stratified composite comprising the steps of:
    combining synthetic fibers and a binder to provide a first fibrous mixture;
    combining crosslinked cellulosic fibers, a superabsorbent polymer and a binder to provide a second fibrous mixture:
    depositing the first fibrous mixture on a foraminous support to form a first stratum;
    depositing the second fibrous mixture on the first fibrous mixture on the foraminous support to form a second stratum thereby providing a stratified fibrous composite, said composite further comprising a transition zone intermediate and coextensive with the first and second strata, the transition zone comprising fibers from the first and second strata commingled substantially uniformly across the composite's width and along the composite's length; and
    heating the stratified fibrous composite to effect thermal bonding between the fibers and binder to provide a unitary stratified composite.

2. The method of claim 1 wherein the step of combining crosslinked cellulosic fibers, superabsorbent polymer, and a binder to provide a second fibrous mixture further comprises combining cellulosic fibers with said crosslinked fibers, superabsorbent polymer, and binder.

3. The method of claim 1 wherein the first fibrous mixture is an aqueous slurry.

4. The method of claim 1 wherein the second fibrous mixture is an aqueous slurry.

5. The method of claim 1 further comprising the step of removing water from the stratified fibrous composite.

6. The method of claim 1 wherein the synthetic fibers are selected from the group consisting of polyethylene terephthalate, polyethylene, polypropylene, nylon, latex, rayon fibers, and mixtures thereof.

7. The method of claim 1 wherein the binder comprises a multicomponent binding fiber.

8. The method of claim 1 wherein the first fibrous mixture and the second fibrous mixture are deposited on the foraminous support substantially simultaneously.

9. The method of claim 1 wherein the first fibrous mixture is deposited by an offset headbox.

10. The method of claim 1 wherein the second fibrous mixture is deposited by an offset headbox.

11. The method of claim 1 wherein the foraminous support is a forming wire.

12. The method of claim 1 wherein the mixing of the fibers of first and second fibrous mixtures is enhanced through the application of vacuum to the foraminous support.

* * * * *